(12) United States Patent
Rolf

(10) Patent No.: US 7,288,265 B1
(45) Date of Patent: Oct. 30, 2007

(54) TREATING VIRAL INFECTION AT SMALLPOX VACCINATION SITE

(75) Inventor: David Rolf, Eden Prairie, MN (US)

(73) Assignee: LecTec Corporation, Edina, MN (US)

( * ) Notice: Subject to any disclaimer, the term of this patent is extended or adjusted under 35 U.S.C. 154(b) by 567 days.

(21) Appl. No.: 10/338,809

(22) Filed: Jan. 8, 2003

Related U.S. Application Data

(63) Continuation-in-part of application No. 09/688,445, filed on Oct. 16, 2000, now abandoned.

(51) Int. Cl.
*A61F 13/00* (2006.01)
*A61L 15/16* (2006.01)

(52) U.S. Cl. .................. 424/449; 424/448; 424/443
(58) Field of Classification Search .............. None
See application file for complete search history.

(56) References Cited

U.S. PATENT DOCUMENTS

| | | | |
|---|---|---|---|
| 4,415,590 A | 11/1983 | Gerzon | 424/319 |
| 4,675,009 A | 6/1987 | Hymes et al. | 604/304 |
| 4,696,854 A | 9/1987 | Ethier | 428/287 |
| 5,536,263 A | 7/1996 | Rolf et al. | 604/307 |
| 5,639,795 A | 6/1997 | Friedman et al. | 514/772.6 |
| 5,741,510 A | 4/1998 | Rolf et al. | 424/448 |
| 5,972,999 A | 10/1999 | Murad | 514/474 |
| 6,231,889 B1 | 5/2001 | Richardson et al. | 424/464 |

OTHER PUBLICATIONS

"External Analgesic Drug Products for Over-the-Counter Human Use; Tentative Final Monograph", *Federal Register*, 48(27), Department of Health and Human Services, Food and Drug Administration, 21 CFR Part 348, (Feb. 1983), pp. 5852-5869.

*Primary Examiner*—Isis Ghali
(74) *Attorney, Agent, or Firm*—Schwegman, Lundberg & Woessner, P.A.

(57) ABSTRACT

An adhesive patch is provided wherein the patch includes a porous backing having a front side and a back side. The patch also includes a therapeutic formulation located on the front side of the backing. The backing includes a flexible sheet of water insoluble porous material. The therapeutic formulation includes a combination of a antiviral agent useful for treating a viral infection in a mammal (e.g., human), a medicament that relieves topical discomfort, an adhesive, and a solvent. The solvent can preferably include a fragrance.

43 Claims, 5 Drawing Sheets

TREATING VIRAL INFECTION AT SMALLPOX VACCINATION SITE

CROSS-REFERENCE TO RELATED APPLICATION

Figure 1:
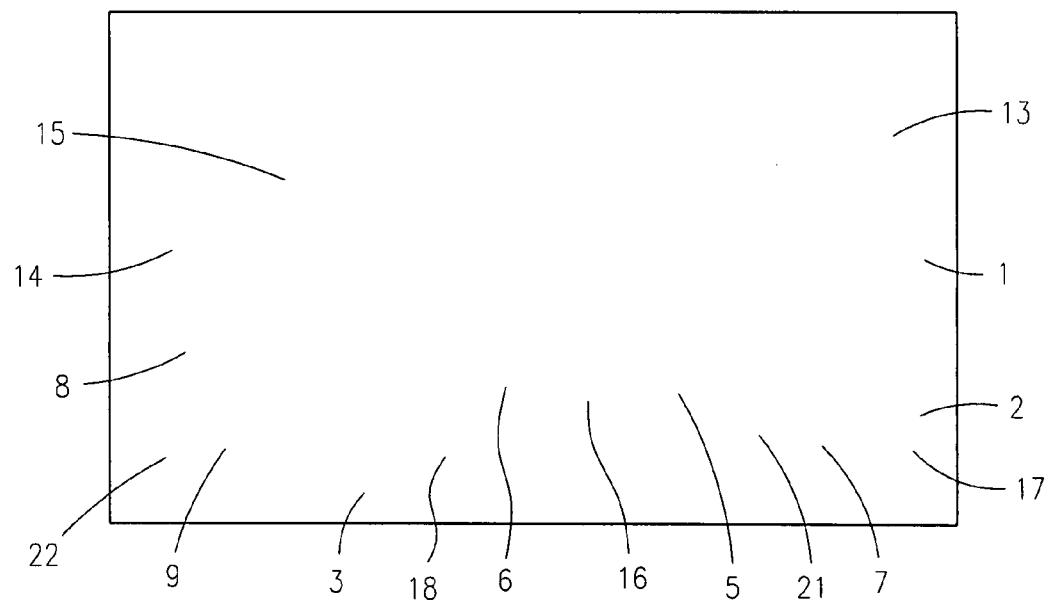
Figure 2:
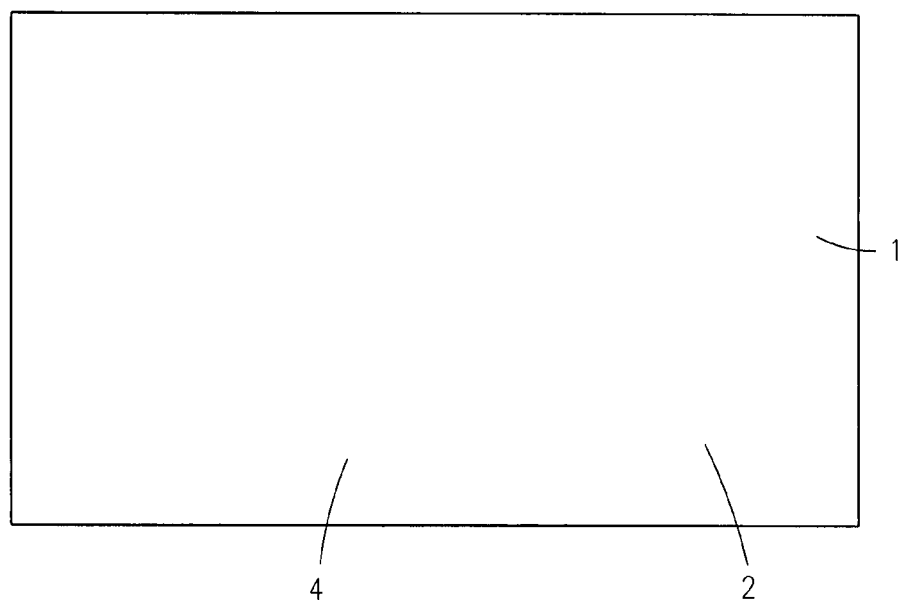
Figure 3:
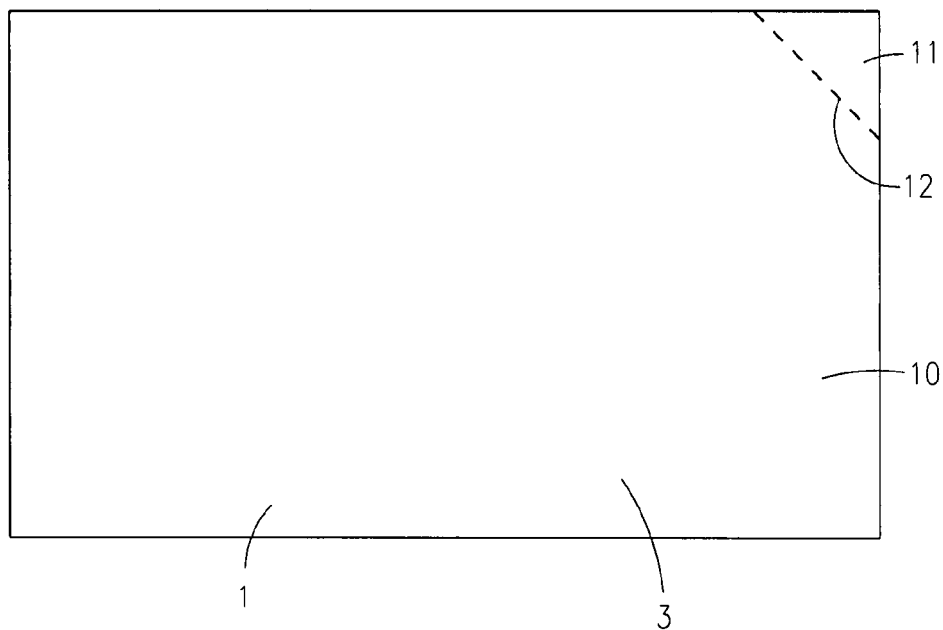
Figure 4:
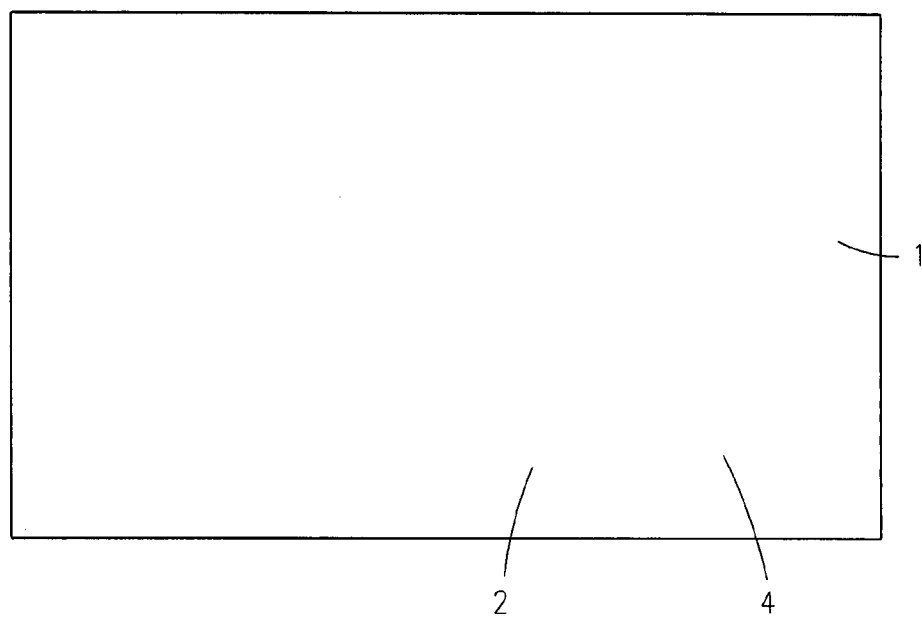
Figure 5:
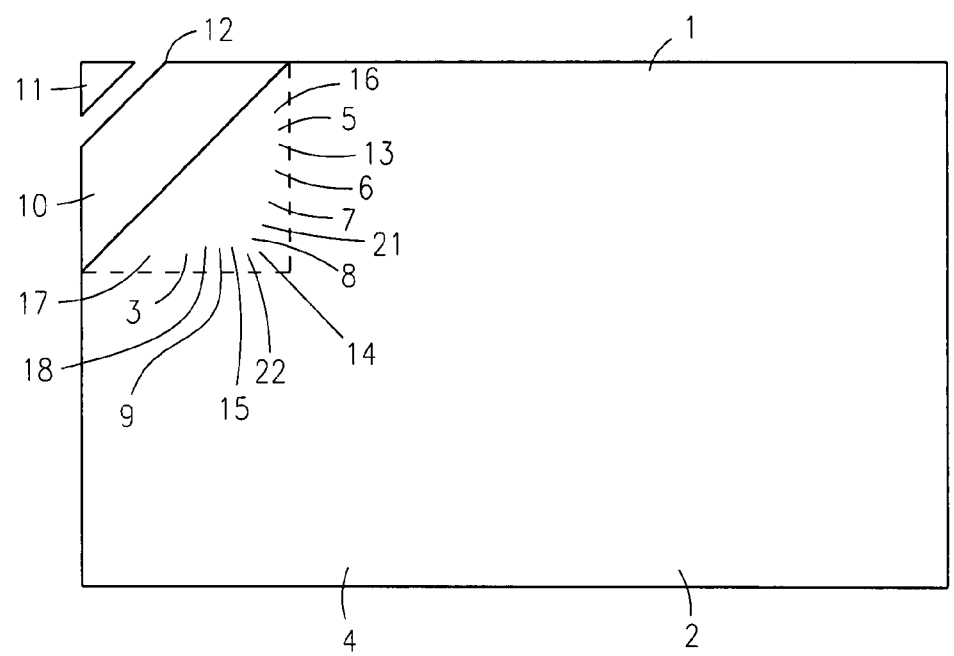
Figure 6:
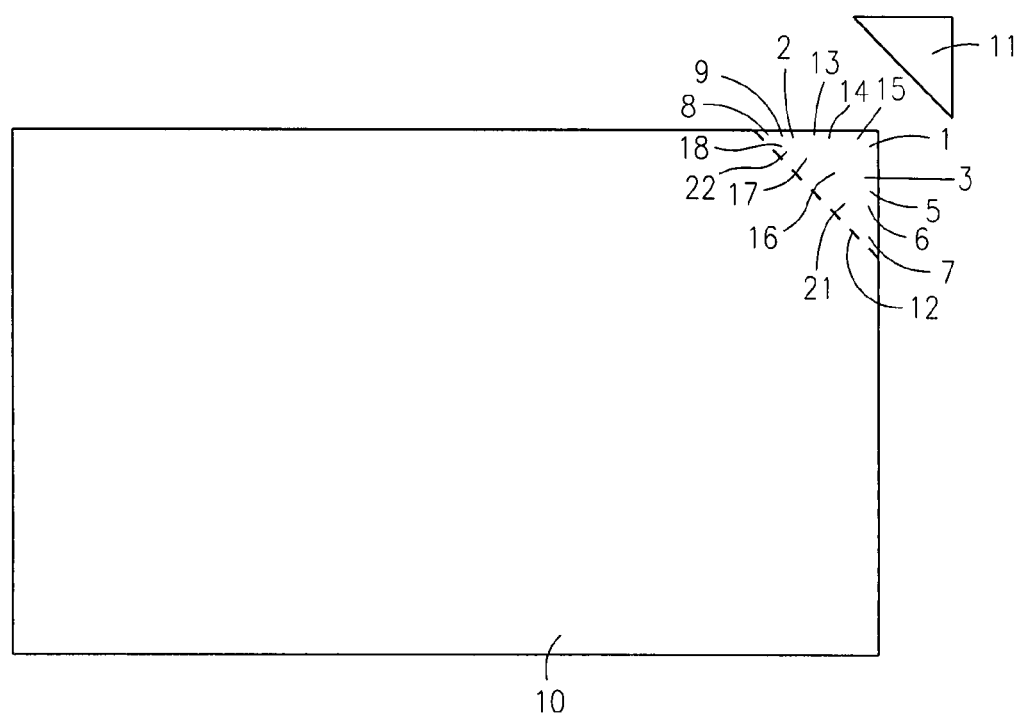

This application is a continuation-in-part (CIP) of U.S. application Ser. No. 09/688,445 filed on 16 Oct. 2000, now abandoned; which is incorporated herein by reference in its entirety.

BACKGROUND OF THE INVENTION

Cold sores are liquid-filled blisters that erupt around the lips and sometimes spread to the nose, chin, eyes, and the skin of the fingers. Cold sores are caused by the herpes simplex virus, type 1 (HSV-1). There are two types of the herpes simplex virus: type 1 (HSV-1), which causes oral herpes and type 2 (HSV-2), which causes genital herpes. Oral herpes manifests itself as cold sores, which are also known as fever blisters.

Most people are infected with HSV-1 by the time they are 10-years-old. Studies in the United States indicate that 30 to 60 percent of children under the age of 10 years have been exposed to HSV-1. The incidence of infection steadily increases with age, reaching 80 to 90 percent among adults 50 years of age and older. Eighty percent of all Americans have the virus that causes cold sores, but only 60 percent have experienced an outbreak. Nearly a quarter of those sufferers experience recurrent outbreaks. Some people do not develop symptoms until months or even years after becoming infected with the virus, and some never experience any symptoms.

HSV-1 is an extremely contagious virus when a sore is present. The virus is spread by direct skin-to-skin contact. Unlike an airborne flu virus, herpes spreads directly from the cold sore to the site of contact. The cold sore is no longer contagious when it has completely healed and the affected skin has returned to normal. The virus usually enters the body through the mouth. The initial contact with the disease does not result in a cold sore, but can be either asymptomatic (no obvious symptoms of infection) or with symptoms more readily associated with an upper respiratory infection, and often lesions in the mouth.

The initial symptoms of an HSV-1 infection usually include burning, tingling, or itching sensations about the edges of the lips or nose within one or two weeks after contact with an infected person. Several hours later, small red papules develop in the irritated area; later small vesicles, or fever blisters, filled with fluid erupt. Several small vesicles may merge to form a larger blister. The vesicles generally are associated with itching, pain, or similar discomfort. Other effects often include a mild fever and enlargement of the lymph nodes in the neck. Laboratory analysis of the vesicular fluid usually shows the presence of herpesvirus particles and the absence of pyogenic bacteria. Within 1 week after the onset of symptoms, thin yellow crusts form on the vesicles as healing begins.

Following the initial episode, the virus moves away from the nerve endings up into portions of the nervous system close to the lips. The HSV-1 virus remains in the body for the remainder of the person's life. What causes approximately one-third of those initially infected to suffer from recurrent cold sores is unknown. However, for those individuals who do suffer from recurrent cold sores, certain factors will initiate the development of a cold sore. These factors include, e.g., colds/flu, emotional stress, fever, sunlight, cold weather and menstruation. The exact mechanism by which trigger factors induce activation of HSV-1 is unknown.

Herpes zoster or shingles is an acute infection caused by reactivation of the latent varicella zoster virus (VZV), which mainly affects adults. It is characterized by the development of painful vesicular skin eruptions that follow the underlying route of cranial or spinal nerves inflamed by the virus.

Distribution of the pain and vesicular eruptions associated with VZT is usually unilateral, although both sides of the body may be involved. Any sensory nerve may be affected, but the virus in most cases tends to invade the posterior root ganglia associated with thoracic and trigeminal nerves. The pain, which may be constant or intermittent, superficial or deep, usually precedes other effects and may mimic that of other disorders, such as appendicitis and or pleurisy. Early symptoms may include gastrointestinal disturbances, malaise, fever, and headache. The vesicles usually evolve from small red macules along the path of a nerve, and the skin of the area is hypersensitive. All of the lesions may appear within a period of hours, but they most often develop gradually over a period of days. The macules vesiculate and after about 3 days, become turbid with cellular debris. Usually at the end of the first week, the vesicles develop crusts. The symptoms may persist for 3 to 5 weeks, but in most cases they diminish after 2 weeks.

Varicella or chickenpox is an acute, highly contagious viral disease caused by a herpesvirus, varicella zoster virus (VZV). It occurs primarily in young children and is characterized by crops of pruritic vesicular eruptions on the skin. The disease is transmitted by direct contact with skin lesions or, more commonly, by droplets spread from the respiratory tract of infected persons, usually in the prodromal period or the early stages of the rash. The vesicular fluid and the scabs are infectious until entirely dry. Indirect transmission through uninfected persons or objects is rare. The diagnosis is usually made by physical examination and by the characteristic appearance of the disease. The virus may be identified by the culture of the vesicle fluid.

The incubation period for chickenpox averages 2 to 3 weeks, followed by slight fever, mild headache, malaise, and anorexia usually occurring 24 to 36 hours before the rash begins. The prodromal period is usually mild in children but may be sever in adults. The rash, which is highly pruritic, begins as macules and progresses in 1 or 2 days to papules, and finally, to vesicles surrounding an erythematous base and containing a clear fluid. Within 24 to 48 hours, the vesicles turn cloudy and become umbilicated, are easily broken, and become encrusted. The lesions, which erupt in crops so that all three stages are present simultaneously, first appear on the back and chest and then spread to the face, neck and limbs; they occur only rarely on the soles and palms. In severe cases, laryngeal or tracheal vesicles in the pharynx, larynx, and trachea may cause dyspnea and dysphagia. Prolonged fever, lymphadenopathy, and extreme irritability from pruritus are other symptoms. The symptoms last from a few days to 2 weeks.

Aphthous stomatitis or a canker sore is an ulcerous lesion of the mouth, characteristic of aphthous stomatitis. Canker sores are a recurring condition characterized by the eruption of painful ulcers on the mucous membranes of the mouth. The cause is unknown, but there is evidence to suggest that aphthous stomatitis is an immune reaction. Heredity, some foods, overenthusiastic tooth brushing, and emotional stress are also possible causes.

Cold sores or fever blisters and shingles can be treated with antiviral medications, including acyclovir, famciclovir and valacyclovir. However, these medications must be repeatedly applied to the infected areas. The medications, which are typically formulated as creams or gels, are messy, unsightly, and inconvenient to the user. In addition, the medications do not treat the symptoms (e.g., burning, tingling, or itching) or secondary infections associated with the cold sores or fever blisters. Chickenpox can be treated with topical antipruritics to relieve the itching and can be treated with antibiotics to treat secondary infections. Again, the medications, which are typically formulated as creams or gels, are messy, unsightly, and inconvenient to the user.

Smallpox is a viral disease with reported death rates in non-immune human populations of approximately 30% (U.S. Centers for Disease Control, Smallpox internet homepage, http://www.bt.cdc.gov/agent/smallpox/overview/disease-facts.as). It is caused by the variola virus (U.S. Centers for Disease Control, Smallpox internet homepage, http://www.bt.cdc.gov/agent/smallpox/overview/disease-facts.as). Historically smallpox caused devastating epidemics throughout the world. However, by 1977 mass immunization against smallpox eradicated the virus that causes the disease in the wild (U.S. Centers for Disease Control, Smallpox internet homepage, http://www.bt.cdc.gov/agent/smallpox/overview/disease-facts.as). Stores of virus were maintained by the United States and the Soviet Union, and possibly other nations. It is believed the virus may now be in the hands of terrorists or states that pose a military threat to the United States and to other nations. These groups and nations might unleash the virus as a weapon against soldiers or civilians. Accordingly, governments are preparing again to vaccinate at least segments of their populations and possibly the general population.

The vaccines planned for use in the United States are based on live strains of a vaccinia virus related to the variola virus that causes smallpox (U.S. Centers for Disease Control, smallpox vaccination page, http://www.bt.cdc.gov/agent/smallpox/vaccination/facts.asp). The vaccinia virus infects other species of mammals and generally causes a localized infection in humans that is not serious, but that results in immunity to smallpox (U.S. Centers for Disease Control, smallpox vaccination page, http://www.bt.cdc.gov/agent/smallpox/vaccination/facts.asp). One such vaccine is DRYVAX™, which is based on vaccinia prepared from the lymph of calves infected with the virus (U.S. Centers for Disease Control, smallpox vaccination page, http://www.bt.cdc.gov/training/smallpoxyaccine/reactions/about_vaccine.htm). To administer the vaccine, a bifurcated needle is dipped in a reconstituted suspension of the virus. The needle is then used to repeatedly puncture the skin of a person being vaccinated (U.S. Centers for Disease Control, smallpox vaccination page, http://www.bt.cdc.gov/training/smallpoxyaccine/reactions/vac_method.htm). If the vaccine "takes," an immune response is elicited. The result is a papule 3-4 days after vaccination. This progresses to a vesicle with surrounding erythema by 5-6 days after vaccination. The vesicle center becomes depressed and progresses to a well-formed pustule by the $8^{th}$ or $9^{th}$ day. By the twelfth day or soon thereafter, the pustule crusts over forming a brown scab. After approximately 3 weeks the scab detaches and a well formed scar remains. (U.S. Centers for Disease Control, smallpox vaccination page, http://www.bt.cdc.gov/training/smallpoxyaccine/reactions/normal.htm.)

Importantly, alcohol cannot be applied to the skin prior to the vaccination to sterilize the skin because this has been shown to inactivate the virus. (U.S. Centers for Disease Control, smallpox vaccination page, http://www.bt.cdc.gov/training/smallpoxyaccine/reactions/vac_method.htm.) Not applying alcohol has the result that the vaccinee is at greater risk that the wound caused by vaccination could be infected with infectious agents present on the skin.

The vaccinia virus infection created by vaccination causes the skin to itch (U.S. Centers for Disease Control, smallpox vaccination page, http://www.bt.cdc.gov/training/smallpoxyaccine/reactions/ery_multi_clinical.htm.). This is a problem because contact with the lesions of the skin can spread the virus to other areas of the body and to other persons. (U.S. Centers for Disease Control, smallpox vaccination page, http://www.bt.cdc.gov/training/smallpoxyaccine/reactions-vacc-public.htm.) Transfer of the virus to the eye or surrounding skin of the vaccinee or other persons is particularly dangerous, because infection with vaccinia in the eye can cause blindness (U.S. Centers for Disease Control, smallpox vaccination page, http://www.bt.cdc.gov/training/smallpoxyaccine/reactions/prevent.htm.). Thus, the vaccinee must be advised to avoid touching or rubbing the vaccination site.

Covering the vaccination site with a sterile gauze is recommended. However, the gauze must be disposed of carefully after use because it contains viable virus and can spread the infection to others or to other areas of the vaccinee. (U.S. Centers for Disease Control, smallpox vaccination page, http://www.bt.cdc.gov/training/smallpoxyaccine/reactions/vac_method.htm.)

The most severe risk associated with vaccination is progressive vaccinia. This occurs in approximately 1-10 persons per 1 million receiving vaccination. (U.S. Centers for Disease Control, smallpox vaccination page, http://www.bt.cdc.gov/training/smallpoxyaccine/reactions/prog_vac.htm.) The virus multiplies at the primary vaccination site causing circumferential expansion of the skin lesion at the site. The virus gains entry to the blood and spreads to distant skin sites and multiple organs. Local and systemic bacterial, fungal, and parasitic infections can ensue. Death caused by toxic or septic shock is likely. (U.S. Centers for Disease Control, smallpox vaccination page, http://www.bt.cdc.gov/training/smallpoxyaccine/reactions/prog_vac_path.htm.) Patients must be hospitalized and are treated with aggressive immunoglobulin therapy. The risk of progressive vaccinia is greater in immune compromised individuals, such as HIV infected persons and cancer patients (U.S. Centers for Disease Control, smallpox vaccination page, http://www.bt.cdc.gov/training/smallpoxyaccine/reactions/prog_vac_path.htm).

Accordingly, immune compromised persons should not receive the smallpox vaccine. However, the possibility of transfer of the virus from vaccinees to others still places immune compromised persons at risk from the vaccine.

A more common risk of vaccination is bacterial infection at the site of vaccination (U.S. Centers for Disease Control, smallpox vaccination page, http://www.bt.cdc.gov/training/smallpoxyaccine/reactions/bac_inf.htm). Staphylococci and streptococci infections are the most likely. Normal skin flora includes staphylococcal and streptococcal species. In addition, in infants fecal contamination of the skin is common. Thus, disruption of the skin by vaccination may provide a fertile field for bacterial superinfection and multiplication (U.S. Centers for Disease Control, smallpox vaccination page, http://www.bt.cdc.gov/training/smallpoxyaccine/reactions/bac_inf.htm). The use of occlusive dressings over the site of vaccination can increase this risk. Tightly bound and occlusive dressings can macerate the skin. They also may lead to more frequent occurrence of infection, anaerobic infection, and more serious disease. (U.S. Centers for Disease Control, smallpox vaccination page, http://www.bt.cdc.gov/training/smallpoxyaccine/reactions/bac_inf.htm.)

Another common side effect of vaccination is generalized vaccinia, which is a benign spreading of the virus through systemic circulation, which leads to lesions on unimmunized skin (U.S. Centers for Disease Control, smallpox vaccination page, http://www.bt.cdc.gov/training/smallpoxyaccine/reactions/gen_vac_clinical.htm).

Another adverse event associated with vaccinia vaccination is erythema multiforme, which is a toxic or allergic skin rash that can be frightening in appearance. Intense itching can accompany the rash, and scratching can lead to bacterial superinfection. Rarely, erythema multiforme develops into desquamating Stevens-Johnson syndrome with full body involvement and conjunctival and corneal inflammation. (U.S. Centers for Disease Control, smallpox vaccination page, http://www.bt.cdc.gov/training/smallpoxyaccine/reactions/ery_multi_clinical.htm)

Hence, methods to treat side effects and adverse events associated with smallpox vaccination are needed. A need exists for treatments to reduce itching and scratching associated with the vaccination, and to prevent or treat superinfection with bacterial, viral, and fungal infectious agents at the vaccination site. A need also exists for treatments to reduce the risk of spreading the vaccinia infection to other persons, or other areas of the body, including the eyes and surrounding skin.

Several topical patch devices have been used for applying medication to the skin. For example, U.S. Pat. No. 4,675,009; U.S. Pat. No. 5,536,263; and U.S. Pat. No. 5,741,510 each describe a drug dispensing device for the delivery of medication to the skin. While the patches disclosed are generally effective in the delivery of a medicament (e.g., topical antitussive) to the skin, there exists a need for water insoluble, protective, adhesive patches that administer effective and known amounts of an antiviral agent, external anesthetic or analgesic, antipruritic, and antimicrobial agent to the skin. The suitable patch should maintain the adhesive properties of the patch and the stability of one or more of the antiviral agent, external anesthetic, analgesic, antipruritic, and antimicrobial agent over a prolonged period of time typically experienced in the manufacturing, packaging, shipping, and/or the storage of the patch (e.g., up to about two years). The suitable patch should be effective in treating cold sores or fever blisters. The suitable patch should also be effective in preventing secondary infections associated with cold sores or fever blisters. In addition, the suitable patch should treat the symptoms (e.g., burning, tingling, or itching) associated with the cold sores or fever blisters. Preferably, the patch will comply with any FDA regulations regarding the one or more of the antiviral agent, external anesthetic, analgesic, antipruritic, and antimicrobial agent. The suitable patch should also administer an effective and known amount of one or more of the antiviral agent, external anesthetic, analgesic, and antipruritic to the skin of the patient.

SUMMARY OF THE INVENTION

The present invention provides a water insoluble, protective, adhesive patch useful for treating cold sores or fever blisters. The patch prevents secondary infections associated with cold sores or fever blisters. The patch treats the symptoms (e.g., burning, tingling, or itching) associated with cold sores or fever blisters. The patch administers to the skin an effective and known amount of an antiviral agent and a medicament useful for relieving topical discomfort. The patch maintains the adhesiveness of the adhesive and the stability of one or more of the antiviral agent, the medicament useful for relieving topical discomfort, and the antimicrobial agent, over a prolonged period of time typically experienced in the manufacturing, packaging, shipping, and/or the storage of the patch. The patch also complies with FDA regulations.

The patch of the present invention is also useful for patients having recently received a vaccination (e.g., smallpox vaccination). The patch absorbs exudate from the vaccination site. The patch prevents viral infections associated with vaccinations. The patch treats symptoms associated with viral infections caused by vaccinations, treats secondary bacterial and fungal infections caused by vaccinations. The patch also prevents cross-contamination of a viral infection from a vaccination site.

The present invention provides an adhesive patch. The patch includes a backing of a flexible sheet of water insoluble material. The backing has a front side and a back side. A therapeutic formulation is positioned on at least a portion of the front side of the backing, is positioned in at least a portion of the front side of the backing, or is positioned on and in at least a portion of the front side of the backing. The therapeutic formulation includes an antiviral agent, a medicament useful for relieving topical discomfort, an antimicrobial agent, an adhesive, and a solvent.

The present invention provides another adhesive patch. The patch includes a backing of a flexible sheet of water insoluble material. The backing has a front side and a back side. A therapeutic formulation is positioned on at least a portion of the front side of the backing, is positioned in at least a portion of the front side of the backing, or is positioned on and in at least a portion of the front side of the backing. The therapeutic formulation includes lysine hydrochloride, lidocaine, camphor, quat-15, an acrylic ester copolymer, karaya, and eucalyptus oil.

The present invention provides another adhesive patch. The patch includes a backing of a flexible sheet of water insoluble material. The backing has a front side and a back side. A therapeutic formulation is positioned on at least a portion of the front side of the backing, is positioned in at least a portion of the front side of the backing, or is positioned on and in at least a portion of the front side of the backing. The therapeutic formulation includes lysine hydrochloride, lidocaine, camphor, quat-15, an acrylic ester copolymer, karaya, an antibiotic agent, and eucalyptus oil.

The present invention provides another adhesive patch. The patch includes a backing of a flexible sheet of water insoluble material. The backing has a front side and a back side. A therapeutic formulation is positioned on at least a portion of the front side of the backing, is positioned in at least a portion of the front side of the backing, or is positioned on and in at least a portion of the front side of the backing. The therapeutic formulation includes lysine hydrochloride, lidocaine, camphor, quat-15, an acrylic ester copolymer, karaya, a skin protectant, and eucalyptus oil.

The present invention also provides a kit. The kit includes an adhesive patch of the present invention and a vaccine.

The present invention also provides a method for treating a viral infection in a mammal (e.g., human). The method includes applying to the skin surface of the mammal having the viral infection or to the skin surface of the mammal at risk thereof an adhesive patch of the present invention.

The present invention also provides a method for absorbing exudate from a viral infection in a mammal. The method includes applying to the skin surface of the mammal having the viral infection or to the skin surface of the mammal at risk thereof an adhesive patch of the present invention.

The present invention also provides a method for treating symptoms associated with viral infections. The method includes applying to the skin surface of the mammal afflicted with the viral infection an adhesive patch of the present invention.

The present invention also provides a method for treating, in a mammal, a secondary bacterial infection associated with a viral infection. The method includes applying to the skin surface of the mammal having the secondary bacterial infection, an adhesive patch of the present invention.

The present invention also provides a method for treating a viral infection caused by a vaccination, in a mammal in need thereof. The method includes applying to the skin surface of the mammal having been vaccinated, an adhesive patch of the present invention.

The present invention also provides a method for absorbing exudate from a viral infection caused by a vaccination, in a mammal in need thereof. The method includes applying to the skin surface of the mammal having been vaccinated, an adhesive patch of the present invention.

The present invention also provides a method for treating symptoms associated with viral infections caused by vaccination. The method includes applying to the skin surface of the mammal having been vaccinated an adhesive patch of the present invention.

The present invention also provides a method for treating, in a mammal, a secondary bacterial infection associated with a viral infection caused by a vaccination. The method includes applying to the skin surface of the mammal having been vaccinated an adhesive patch of the present invention.

The present invention also provides a method for preventing cross-contamination of a viral infection from a vaccination site. The method includes applying to the skin surface of the mammal having been vaccinated, an adhesive patch of the present invention.

The present invention also provides a method for preventing cross-contamination of a viral infection from a vaccination site. The method includes applying to the skin surface of the mammal having been vaccinated, an adhesive patch that includes a backing of a flexible sheet of water insoluble material. The backing has a front side and a back side. A therapeutic formulation is positioned on at least a portion of the front side of the backing, is positioned in at least a portion of the front side of the backing, or is positioned on and in at least a portion of the front side of the backing. The therapeutic formulation includes an adhesive and a solvent.

The present invention also provides a method for absorbing exudate from a viral infection caused by a vaccination, in a mammal in need thereof. The method includes applying to the skin surface of the mammal having been vaccinated, an adhesive patch that includes a backing of a flexible sheet of water insoluble material. The backing has a front side and a back side. A therapeutic formulation is positioned on at least a portion of the front side of the backing, is positioned in at least a portion of the front side of the backing, or is positioned on and in at least a portion of the front side of the backing. The therapeutic formulation includes an adhesive and a solvent.

The present invention also provides a method for treating a vaccinated skin surface afflicted with raised bumps filled with a thick opaque fluid. The method includes applying to the skin surface of the mammal having been vaccinated and afflicted with the raised bumps, an adhesive patch of the present invention that includes a liquid-soluble solute dissolved in the therapeutic formulation in a sufficient quantity such that the osmotic pressure of the therapeutic formulation is above about 308 mOsmol/L, for a period of time effective for the fluid contained in the raised bumps to be transported by osmotic pressure into the therapeutic formulation, thereby reducing accumulated fluid contained in the raised bumps, while keeping the epidermis intact. During such a method, the therapeutic formulation can be maintained in a hypertonic state relative to the raised bumps.

The present invention also provides a kit. The can include a patch of the present invention and a vaccine. The vaccine can be a pox type virus (e.g., smallpox, cowpox, or monkeypox). The small pox vaccine can be DRYVAX. The vaccine can be located in a syringe. Alternatively, vaccine can be located in a vial. The vaccine can be a single unit dosage of a vaccinia virus or a multiple unit dosage of a vaccinia virus. Additionally, the kit can further include instructions.

The present invention also provides another kit. The kit can include multiple patches of the present invention. Each of the patches can independently be the same or different. Such a kit would allow a different patches to be used on the vaccination site depending upon the need. For example, one patch could have anti-itch ingredients for days 2 through 5, hypertonicity for days 2 through 10 and anti-viral compounds from days 10 through 21. The kit can include, e.g., up to about 30 patches, up to about 20 patches, or up to about 10 patches. The kit can also include directions or instructions specifying which patch to administer to the patient on a specified day after the patient has received the vaccination.

BRIEF DESCRIPTION OF THE DRAWINGS

FIG. 1 illustrates the front side of an adhesive patch of the present invention.

FIG. 2 illustrates the back side of an adhesive patch of the present invention.

FIG. 3 illustrates the front side of an adhesive patch of the present invention with a release liner attached to the patch.

FIG. 4 illustrates the back side of an adhesive patch with a release liner attached to the patch.

FIG. 5 illustrates the back side of an adhesive patch of the present invention with a release liner attached to the patch, wherein the patch is partially detached from the release liner.

FIG. 6 illustrates the back side of an adhesive patch of the present invention with a release liner attached to the patch, wherein the patch is partially detached from the release liner.

FIG. 7 illustrates a top view of a specific patch of the present invention.

FIG. 8 illustrates a top view of a specific patch of the present invention.

FIG. 9 illustrates a specific patch of the present invention in use.

FIG. 10 illustrates an enlarged cross-sectional view of specific patch of the present invention.

FIG. 11 illustrates a specific patch of the present invention in use.

DETAILED DESCRIPTION OF THE INVENTION

The present invention provides a unique adhesive vehicle. The vehicle has pressure sensitive adhesive qualities due to its composition and viscoelastic nature. The adhesive formulation is hydrophilic and therefore, water can dissolve into or evaporate from the adhesive, depending on the conditions to which it is exposed. This water exchange capability implies that if the adhesive formulation is on, e.g., a suitably porous backing and is applied to the skin, it will not be occlusive as most drug delivery patches are. The occlusive nature of conventional drug delivery patches is thought to play an important role in enhancing drug absorption, but also often results in greater incidence of skin irritation. The relatively low occlusiveness of the a specific adhesive patch in a specific embodiment of the present invention can be envisioned to be a special adhesive ointment or gel which is water-breathable, such as a water washable or water soluble ointment or gel.

The present invention provides an ointment or gel on a backing. The ointment or gel can include an effective, known, and safe amount of an antiviral agent, a medicament useful for relieving topical discomfort, and an antimicrobial agent. The backing is pliable and/or stretchable. Since the backing can be porous and/or vapor permeable, many consumers typically refer to the device as a "patch," a "skin patch," or an "adhesive skin patch." As such, the device (i.e., the ointment or gel on the backing) will herein be referred to as a patch, a skin patch, an adhesive skin patch and/or as a smallpox patch. It is appreciated that those skilled in the art understand that the term "patch" is used to refer to the device and is not otherwise limiting in any manner.

As used herein, "holdout" refers to the physical properties of a backing, relating to the ability of a specific class of gels or ointments to penetrate, cross-link, wet, and/or cure within the matrix of the backing. A specific class of gels or ointments may or may not be able to penetrate a given backing. Upon penetration of a gel or ointment into a backing, the gel or ointment will cross-link, wet, or cure in the backing. As such, the holdout properties are the ability of the gel or ointment to affect the degree of penetration, cross-linking, wetting, and/or curing within the matrix of the backing. Those backings with superior holdout properties will typically prevent, decrease, or lessen the likelihood of the ointment or gel from wetting the backing; will typically increase the likelihood of the ointment or gel to cross-link within the matrix of the backing; will typically increase the likelihood of the ointment or gel to cure within the matrix of the backing; and/or will typically prevent, decrease, or increase the likelihood of the ointment or gel to partially penetrate the matrix of the backing.

Referring to FIGS. 1-10, an adhesive patch 1 of the present invention is provided.

Backing

The backing 2 is defined by front side 3 (the side exposed to the skin during use) and a back side 4 (the side exposed to the environment during use). The backing 2 should be nonirritating to human skin. The backing 2 is a self-supporting sheet of water soluble or water insoluble, polymeric or natural material that provides strength and integrity for the formulation 5. The backing 2 of the adhesive patch 1 can be vapor permeable. The backing 2 can also be porous, since porosity provides openings for receiving the formulation 5 and it helps to assure that the adhesive skin patch 1 is vapor permeable. Specifically, the backing 2 can retain the formulation 5 while allowing moisture from the skin to pass. Alternatively, the backing 2 can be non-porous. The backing 2 can have any suitable thickness, provided the suitable thickness allows for a flexible, bendable, pliable, vapor permeable, and/or a stretchable sheet of water insoluble porous material. Specifically, the thickness of the backing 2 can be about 0.001 mm to about 5.0 mm, about 0.001 mm to about 3.0 mm, or about 0.025 mm to about 1.25 mm.

The backing 2 can be manufactured from any suitable material, provided the suitable material can form a flexible, bendable, pliable, and/or stretchable backing 2. The backing 2 includes a flexible porous or non-porous sheet of water soluble or water insoluble material that provides support for the adhesive skin patch 1. The backing 2 can include water soluble or water insoluble polymeric fibers, a porous film, or any other kind of matrix with spaces within the matrix. A specific backing 2 is a lightweight, porous, pliable strip composed of a nonwoven fabric of polymeric or natural fibers such as polyester, cotton or cellulose fibers bonded together with a sizing resin. The backing 2 can be woven or nonwoven. Preferably, the backing 2 includes nonwoven fabric. Specifically, the backing 2 can include polyester fibers, polyurethane fibers, polyolefin fibers, polyamide fibers, natural fibers, cotton fibers, copolyester, copolyester fibers, cellulose acetate fibers, polycellulose fibers, or any mixture thereof. Additional stable, water insoluble flexible sheet materials and methods for manufacturing the suitable backings 2 are disclosed, e.g., in U.S. Pat. No. 4,675,009; U.S. Pat. No. 5,536,263; U.S. Pat. No. 4,696,854; U.S. Pat. No. 5,741,510, and references cited therein, and are suitable as backings 2 according to the present invention. The infusion of the formulation 5 into the backing 2 can be accomplished, e.g., with the use of a continuous process mixer, as disclosed, e.g., in U.S. Pat. No. 5,536,263, and references cited therein; or as discussed herein.

Alternatively, the backing 2 can be a non-woven backing 2 that is treated by coating: the front side 3 of the backing 2, the back side 4 of the backing 2, or both the front side 3 and back side 4 of the backing 2; with a silicone-containing compound, a fluorocarbon solution, or a combination thereof. Suitable silicone-containing compounds include, e.g., polydimethyl siloxanes, dialkylsiloxanes, dimethylsiloxo vinyl alkenes, dialkylsiloxo vinyl alkenes, dimethylsiloxo acrylates, dialkylsiloxo acrylates, vinyl terminated polydimethylsiloxane, and vinyl terminated polydialkylsiloxane. The exemplary silicone-containing compounds are commercially available from, e.g., Goldschmidt Chemical Corp. (Essen, Germany); GE Silicones (Waterford, N.Y.); Wacker Silicone Corp. (Adrian, Mich.); and Dow Corning Corp. (Midland, Mich.).

The backing 2 can be manufactured from a suitable non-woven fabric that is commercially available from, e.g., Freudenberg Faservliesstoffe KG (Weinham, Germany); Sontara Technologies (division of DuPont Corporation) (Old Hickory, Tenn.); Lystil S. A. (Brignoud Cedex, France); Dexter Nonwovens (Windsor Locks, Conn.); and Chicopee (New Brusnwick, N.J.). Other commercial vendors that supply suitable non-woven fabrics can be found at the Technical Textile website (http://www.technical-textiles.net/technical-textiles-index/orgL.htm).

The use of a treated backing, such as a fluorocarbon treated non-woven backing, typically increases the yield of an adhesive skin patch 1 of the present invention. The use of a backing material that has been treated with a sizing agent allows for the effective control of the rate of penetration, such that the gel or ointment has solidified after it has begun to penetrate the backing, but before it has passed completely through the backing. In addition, the use of a backing material that has been treated with a sizing agent allows for the effective control of the depth to which the ointment or gel will easily penetrate before solidifying. Increasing the control of the rate at which the ointment or gel penetrates the backing typically improves the overall yield of the production process by reducing the amount of material which must be discarded because the back side of the backing has become too tacky for either processing or for consumer acceptance.

At least a portion of the backing 2 can be treated with a sizing agent 20 such that the portion of the backing 2 that is treated with the sizing agent 20 has a surface energy of about 20 dynes/cm$^2$ to about 65 dynes/cm$^2$. Specifically, the portion of the backing 2 that is treated with the sizing agent 20 can have a surface energy of about 27 dynes/cm$^2$ to about 56 dynes/cm$^2$. The sizing agent 20 lowers the surface energy of the portion of the backing 2 that is treated with the sizing agent 20. Any suitable sizing agent 20 can be employed, provided the portion of the backing 2 that is treated with the sizing agent 20 has a surface energy of about 20 dynes/cm$^2$ to about 65 dynes/cm$^2$. Suitable sizing agents 20 include, e.g., fluorocarbon solutions, silicone-containing compounds, and combinations thereof. Specifically, the backing 2 can be a non-woven backing 2 that is treated with a fluorocarbon. For example, the fluorocarbon treated backing 2 can be, e.g., Vilmed M1585 W/HY, Vilmed M1585H/HY, Vilmed M1586 W/HY, Vilmed M1586H/HY, Vilmed M1570, Vilmed M1573 F, Vilmed M1573 FH, Vilmed M1577 F, Vilmed M1578 F, or Vilmed M1578 FH; which are all commercially available from Freudenberg Faservliesstoffe KG (Weinham, Germany). Alternatively, the silicone treated backing 2 can be a non-woven backing 2 that is coated with one or more silicone-containing compounds, e.g., a polydimethyl siloxane, a dialkylsiloxane, a dimethylsiloxo vinyl alkene, a dialkylsiloxo vinyl alkenes, a dimethylsiloxo acrylate, a dialkylsiloxo acrylate, a vinyl terminated polydimethylsiloxane, and a vinyl terminated polydialkylsiloxane.

At least a portion of the backing 2 can be treated with the sizing agent 20. The portion of the backing 2 that is treated with the sizing agent 20 can be that portion of the backing 2 that can typically include the formulation 5. The entire surface of the front side 3 of the backing 2 can be treated with the sizing agent 20 or a portion of the surface of the front side 3 of the backing 2 can be treated with the sizing agent 20. Preferably, the entire surface of the front side 3 of the backing 2 can be treated with the sizing agent 20. In addition to the surface of the front side 3 of the backing 2 being treated with the sizing agent 20, the sizing agent 20 can penetrate at least a portion of the underlying surface (e.g., one-tenth to about nine-tenths the thickness, or about one-fourth to about nine-tenths the thickness) of the backing 2. Specifically, the sizing agent 20 can penetrate the entire underlying surface of the backing 2.

Suitable fluorocarbon solutions include, e.g., Vilmed M1585 W/HY™, Vilmed M1585H/HY™, Vilmed M1586 W/HY™, Vilmed M1586H/HY™, Vilmed M1570™, Vilmed M1573 F™, Vilmed M1573 FH™, Vilmed M1577 F™, Vilmed M1578F™, and Vilmed M1578 FH™; which are all commercially available from Freudenberg Faservliesstoffe KG (Weinham, Germany).

Alternatively, the fibers of the backing 2 can be interlocked mechanically by air or water.

As shown in FIGS. 1-6 and 9-10, the backing 2 includes a front side 3 and a back side 4. The adhesive skin patch 1 includes a formulation 5 located in at least a portion of the front side 3 of the backing 2, on at least a portion of the front side 3 of the backing 2, or on and in at least a portion of the front side 3 of the backing 2. As such, the formulation 5 can be located on the entire surface of the front side 3 of the backing 2 or the formulation 5 can be located on a portion of the surface of the front side 3 of the backing 2.

Preferably, the formulation 5 can be located on the entire surface of the front side 3 of the backing 2. In addition to being located on the surface of the front side 3 of the backing 2, the formulation 5 can be located in at least a portion of the underlying surface of the front side 3 of the backing 2 (i.e., the formulation 5 can be partially embedded into the backing 2).

Figure 9:
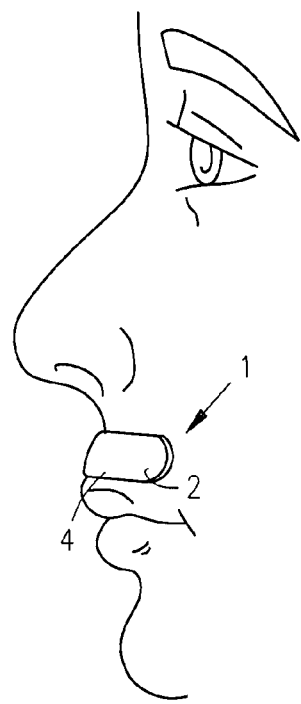
Figure 10:
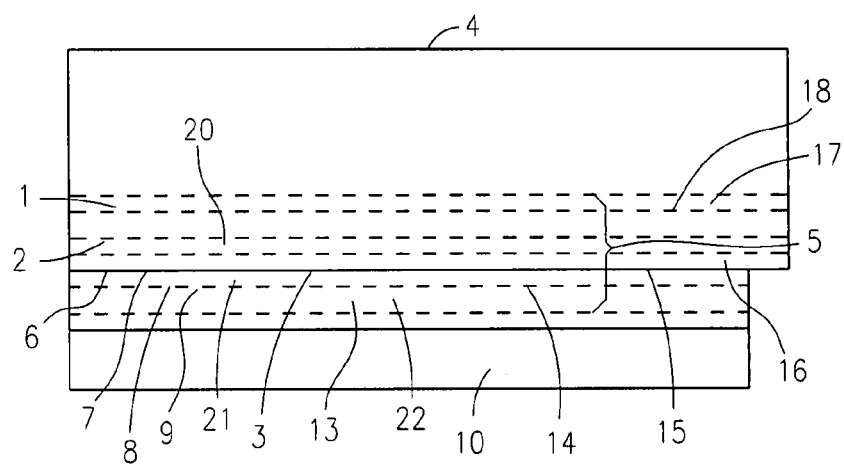

As shown in FIG. 9, the formulation 5 can penetrate a substantial portion of the front side 3 of the backing 2, as disclosed, e.g., in U.S. Pat. No. 5,536,263, and references cited therein. For example, the formulation 5 can penetrate about one-tenth to about nine-tenths the thickness of the backing 2, or about one-fourth to about nine-tenths the thickness of the backing 2. As such, the formulation 5 can be partially embedded into the backing 2. Preferably, the formulation 5 can be located on the entire front side 3 of the backing 2 and partially in the front side 3 of the backing 2 (i.e., the formulation 5 is partially embedded into the backing 2).

Alternatively, a portion of the front side 3 of the backing 2 can include the formulation 5 and other portions of the front side 3 of the backing 2 can include any combination of the pressure sensitive adhesive 14 and solvent 13. For example, a central circular portion of the front side 3 of the backing 2 can include the formulation while the remaining portions of the front side 3 of the backing 2 include only the pressure sensitive adhesive 14. The formulation 5, when partially embedded into the front side 3 of the backing 2, imparts strength and structure into the adhesive patch 1. For example, when the formulation 5 is partially embedded into the backing 2, the likelihood that the adhesive patch 1 will tear apart when separated from the release liner 10 or when removed from the skin after use, is minimized.

When the adhesive skin patch 1 is placed upon the skin of a patient (e.g., human), the formulation 5 can be in continuous contact with the skin surface of the patient.

Preferably, the adhesive skin patch 1, upon contact with skin, will allow the skin to breathe. More preferably, the adhesive skin patch 1, upon prolonged contact with skin, will hold in place the formulation 5 and will permit the skin to breathe over prolonged periods of time typically experienced with the use of the patch, e.g., up to about 7 days, up to about 24 hours, up to about 12 hours, up to about 8 hours, or up to about 6 hours.

As shown in FIGS. 3-6 and 9, the adhesive skin patch 1 can be reversibly attached to a release liner 10. The release liner 10 helps to maintain the adhesiveness of the adhesive skin patch 1 prior to use, such as during manufacturing, packaging, shipping, and/or storage. Any suitable release liner 10 can be employed for use in the present invention. Suitable release liners 10 are readily known to those of skill in the art. See, e.g., U.S. Pat. No. 4,675,009; U.S. Pat. No. 5,536,263; U.S. Pat. No. 4,696,854; U.S. Pat. No. 5,741,510, and references cited therein for further descriptions of release liners 10 useful in the present invention. The release liner 10 can include a perforation 12 that allows the tab section 11 of the release liner 10 to be removed (see, FIGS. 3, 5, and 6). Removal of the tab section 11 of the release liner 10 allows the adhesive skin patch 1 to be removed from the release liner 10 with relative ease.

Preferably, the patch 1, upon contact with skin, will allow the skin to breathe. More preferably, the patch 1, upon prolonged contact with skin, will hold in place the therapeutic formulation 5 and will permit the skin to breathe over prolonged periods of time typically experienced with the use of the patch, e.g., up to about 7 days, up to about 24 hours, up to about 12 hours, up to about 8 hours, or up to about 6 hours.

The backing 2 is a porous or non-porous, self-supporting sheet of water insoluble or water soluble, polymeric or natural material that provides strength and integrity for the therapeutic formulation 5. For example, the backing 2 can be water insoluble polymeric fibers, open cell foam backing (e.g., polyurethane, polyvinyl chloride, or polyethylene), a porous film, or any other kind of matrix with spaces within the matrix. Preferably, the backing 2 can include polyester, polyurethane, polyolefin, polyamide fibers, natural fibers, cotton fibers, polycellulose fibers, or any mixture thereof.

A specific backing 2 is a lightweight, porous, pliable strip composed of a nonwoven fabric of polymeric or natural fibers such as polyester, cotton or cellulose fibers bonded together with a sizing resin. Additional stable, water insoluble flexible sheet materials are disclosed, e.g., in U.S. Pat. No. 4,675,009; U.S. Pat. No. 5,536,263; U.S. Pat. No. 4,696,854; U.S. Pat. No. 5,741,510, and references cited therein, and are suitable as backings according to the present invention. The infusion of the therapeutic formulation 5 into the backing 2 can be accomplished with the use of a continuous process mixer, as disclosed, e.g., in U.S. Pat. No. 5,536,263, and references cited therein.

As shown in FIGS. 3-6 and 10, the patch 1 is preferably reversibly attached to a release liner 10. The release liner 10 helps to maintain the adhesiveness of the patch 1 prior to use, such as during manufacturing, packaging, shipping, and/or storage. Any suitable release liner 10 can be employed for use in the present invention. Suitable release liners 10 are readily known to those of skill in the art. See, e.g., U.S. Pat. No. 4,675,009; U.S. Pat. No. 5,536,263; U.S. Pat. No. 4,696,854; U.S. Pat. No. 5,741,510, and references cited therein for further descriptions of release liners 10 useful in the present invention. The release liner 10 can include a perforation 12 that allows the tab section 11 of the release liner 10 to be removed (see, FIGS. 3, 5, and 6). Removal of the tab section 11 of the release liner 10 allows the patch 1 to be removed from the release liner 10 with relative ease.

Therapeutic Formulation

As shown in FIGS. 1-6 and 10, the backing 2 includes a front side 3 and a back side 4. The patch 1 includes a therapeutic formulation 5 located in at least a portion of the front side 3 of the backing 2, located on at least a portion of the front side 3 of the backing 2, or located on and in at least a portion of the front side 3 of the backing 2. Preferably, the therapeutic formulation 5 is located on the entire front side 3 of the backing 2 and partially in the front side 3 of the backing 2 (i.e., the therapeutic formulation 5 is partially embedded into the backing 2).

The therapeutic formulation 5 can be positioned on and in any portion of the front side 3 of the backing 2. The therapeutic formulation 5 can be positioned in a portion of the front side 3 of the backing 2 (i.e., the therapeutic formulation 5 penetrates a substantial portion of the front side 3 of the backing 2) as disclosed in, e.g., U.S. Pat. No. 5,536,263, and references cited therein. For example, the therapeutic formulation 5 can penetrate a substantial portion of the front side 3 of the backing 2, e.g., typically between about one-fourth to about nine-tenths the thickness of the backing 2. The penetration of the therapeutic formulation 5 into the backing 2 can be seen in FIG. 10.

Preferably, the therapeutic formulation 5 can be positioned on the entire front side 3 of the backing 2. In this latter configuration, the therapeutic formulation 5 will be in continuous contact with the entire front side 3 of the backing 2. When the adhesive skin patch 1 is placed upon the skin surface of a patient, the therapeutic formulation 5 will be in continuous contact with the skin surface of the patient.

Alternatively, a portion of the front side 3 of the backing 2 can contain the therapeutic formulation 5 and other portions of the front side 3 of the backing 2 can contain any combination of the adhesive 14, antiviral agent 15, and solvent 13. For example, a central circular portion of the front side 3 of the backing 2 can contain the therapeutic formulation 5 while the remaining portions of the front side 3 of the backing 2 contains only the adhesive 14.

The therapeutic formulation 5 includes a combination of an antiviral agent 15 useful for treating viral infections in a mammal; a medicament 6 useful for treating topical discomfort (i.e., the symptoms of burning, tingling, and/or itching); an antimicrobial agent 7 useful for preventing bacterial growth, mold growth, fermentation, and/or decomposition; an adhesive 14; and a solvent 13.

The therapeutic formulation 5 can preferably remain stable over the period of time typically experienced with the manufacturing, packaging, shipping, and/or storage of the adhesive skin patch 1, e.g., up to about a month, up to about a year, or up to about two years. The stability of the antiviral agent 15, for example, is due in part to the therapeutic formulation 5 including the antiviral agent 15 in an adhesive formulation. The adhesive formulation is preferably a hydrogel that holds the antiviral agent 15 in an available form while maintaining the necessary stability, pressure sensitive adhesion and effectiveness over prolonged periods of time.

Antiviral Agent

As used herein, an "antiviral agent" is a compound or combination of compounds that weakens or abolishes the action of a virus. *Stedman's Medical Dictionary,* 25th Ed., illustrated, Williams & Wilkins, Baltimore, Md., p. 101 (1990). Any suitable antiviral agent 15 can be employed, provided the antiviral agent 15 effectively treats a viral infection and the antiviral agent 15 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1.

Suitable antiviral agents are disclosed, e.g., in *Physician's Desk Reference* (PDR), Medical Economics Company (Montvale, N.J.), (53rd Ed.), 1999; *Mayo Medical Center Formulary, Unabridged Version,* Mayo Clinic (Rochester, Minn.), January 1998; *Merck Index,* An Encyclopedia of Chemicals, Drugs, and *Biologicals,* (11th Ed.), Merck & Co., Inc. (Rahway, N.J.), 1989; and references cited therein. Suitable antiviral agents 15 include, e.g., zinc, lysine, foscamet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, viracea2, cytovene, famciclovir, valaciclovir, penciclovir, nonoxynol-9, pharmaceutically acceptable salts thereof, and combinations thereof. Additional suitable antiviral agents 15 include, e.g., a hypochloride, a hypochloride generating compound, a peroxide, a peroxide generating compound, an organic halide, an organic halide generating compound, or a combination thereof.

In a specific embodiment of the present invention, the antiviral agent 15 can include lysine hydrochloride.

The antiviral agent 15 can be present in any appropriate and suitable amount, provided the amount of antiviral agent 15 is effective to treat a viral infection and the amount of antiviral agent 15 remains stable in the therapeutic formulation 5 over a prolonged period of time. Typically, the antiviral agent 15 can be present in about 0.01 wt. % to about 99.9 wt. % of the therapeutic formulation 5. The amount of antiviral agent 15 present in the therapeutic formulation 5 will typically depend upon the specific compound or compounds employed as the antiviral agent 15. For example, lysine hydrochloride can be present up to about 99.9 wt. % of the therapeutic formulation 5, up to about 50 wt. % of the therapeutic formulation 5, or up to 20 wt. % of the therapeutic formulation 5. Preferably, the amount of antiviral agent 15 employed in the therapeutic formulation 5 will comply with FDA regulations.

Specifically, lysine hydrochloride can be present up to about 10.0 wt. % of the therapeutic formulation 5. Preferably, lysine hydrochloride can be present up to about 4.0 wt. % of the therapeutic formulation 5. More preferably, lysine hydrochloride can be present in about 0.01 wt. % to about 10.0 wt. % or in about 0.1 wt. % to about 4.0 wt. % of the therapeutic formulation 5.

The antiviral agent 15 can preferably be located on and in any portion of the therapeutic formulation 5, which is located on the front side 3 of the backing 2. Preferably, the antiviral agent 15 can be located on and in the entire portion of the therapeutic formulation 5. When the adhesive skin patch 1 is placed upon the skin of a patient (e.g., human), the antiviral agent 15 can be in continuous contact with the skin surface of the patient.

Medicament Useful for Treating Topical Discomfort

As used herein, topical discomfort includes any of the symptoms associated with viral infections. Such symptoms include, e.g., pain, itching, tingling, and a burning sensation.

The medicament 6 useful for treating topical discomfort can be an analgesic, an antipruritic, an anesthetic, or any combination thereof. As used herein, an "analgesic" is a topically (i.e., externally) applied agent that relieves pain by altering perception of nociceptive stimuli without producing anesthesia or loss of consciousness; an "antipruritic" is a topically (i.e., externally) applied agent that prevents or relieves itching; and an "anesthetic" is a topically (i.e., externally) applied agent that can reversibly depress neuronal function, producing loss of ability to perceive pain and/or other sensations (see, *Stedman's Medical Dictionary*, 25th Ed., III., 1990, p. 65, p. 77, and p. 99).

Any suitable analgesic, antipruritic, and/or anesthetic can be employed, provided the analgesic, antipruritic, and/or anesthetic effectively alleviates topical discomfort and the analgesic, antipruritic, and/or anesthetic remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. Suitable analgesics, antipruritic, and anesthetics are disclosed, e.g., in Federal Register, Vol. 48, No. 27, §348, and references cited therein.

Suitable exemplary analgesics, antipruritics, and/or anesthetics include camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, hydrocortisone acetate, camphorated metacresol, and combinations thereof.

Specifically, the external anesthetic can be lidocaine, which is commercially available from Hawkins Chemical (Minneapolis, Minn.), and camphor, which is commercially available from Jiangsu High Hope (Waxi City, China).

The medicament 6 can be present in any suitable amount provided the medicament 6 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. The medicament 6 can be present in about 0.01 wt. % to about 99.9 wt. % of the therapeutic formulation 5. Preferably, the amount will comply with FDA regulations.

Typically, the amount of medicament 6 present in the therapeutic formulation 5 will depend upon the specific compound or compounds employed as the medicament 6. For example, camphor can be present in about 0.1 to about 3.0 wt. % of the therapeutic formulation 5. Menthol can be present in about 0.1 to about 1.0 wt. % of the therapeutic formulation 5. Benzocaine can be present in about 5.0 wt. % to about 20.0 wt. % of the therapeutic formulation 5. Butamben picrate can be present in about 1.0 wt. % of the therapeutic formulation 5. Dibucaine can be present in about 0.25 wt. % to about 1.0 wt. % of the therapeutic formulation 5. Dibucaine hydrochloride can be present in about 0.3 wt. % to about 0.5 wt. % of the therapeutic formulation 5. Dimethisoquin hydrochloride can be present in about 0.3 wt. % to about 0.5 wt. % of the therapeutic formulation 5. Dyclonine hydrochloride can be present in about 0.5 wt. % to about 1.0 wt. % of the therapeutic formulation 5. Lidocaine can be present in about 0.5 wt. % to about 4.0 wt. % of the therapeutic formulation 5. Lidocaine hydrochloride can be present in about 0.5 wt. % to about 4.0 wt. % of the therapeutic formulation 5. Pramoxine hydrochloride can be present in about 0.5 wt. % to about 1.0 wt. % of the therapeutic formulation 5. Tetracaine can be present in about 1.0 wt. % to about 2.0 wt. % of the therapeutic formulation 5. Tetracaine hydrochloride can be present in about 1.0 wt. % to about 2.0 wt. % of the therapeutic formulation 5. Benzyl alcohol can be present in about 10.0 wt. % to about 33.0 wt. % of the therapeutic formulation 5. Juniper tar can be present in about 1.0 wt. % to about 5.0 wt. % of the therapeutic formulation 5. Phenolate sodium can be present in about 0.5 wt. % to about 1.5 wt. % of the therapeutic formulation 5. Resorcinol can be present in about 0.5 wt. % to about 3.0 wt. % of the therapeutic formulation 5. Diphenhydramine hydrochloride can be present in about 1.0 wt. % to about 2.0 wt. % of the therapeutic formulation 5. Tripelennamine hydrochloride can be present in about 0.5 wt. % to about 2.0 wt. % of the therapeutic formulation 5. Hydrocortisone can be present in about 0.25 wt. % to about 1.0 wt. % of the therapeutic formulation 5. Phenol can be present in about 0.5 wt. % to about 1.5 wt. % of the therapeutic formulation 5. Hydrocortisone acetate can be present in about 0.25 wt. % to about 1.0 wt. % of the therapeutic formulation 5. Camphorated metacresol can be present such that camphor is present in about 3.0 wt. % to about 10.8 wt. % of the therapeutic formulation 5 and metacresol is present in about 1.0 to about 3.6 wt. % of the therapeutic formulation 5.

Preferably, lidocaine can be present to relieve topical discomfort. More preferably, lidocaine can be present in about 1.0 wt. % to about 10.0 wt. % of the therapeutic formulation 5, in about 2.0 wt. % to about 5.0 wt. % of the therapeutic formulation 5, or in bout 3.5 wt. % to about 4.5 wt. % of the therapeutic formulation 5.

Preferably, camphor can be present as the medicament 6. More preferably, camphor can be present in about 0.5 wt. % to about 10.0 wt. % of the therapeutic formulation 5, in about 1.0 wt. % to about 6.0 wt. % of the therapeutic formulation 5, or in bout 1.5 wt. % to about 3.0 wt. % of the therapeutic formulation 5.

The medicament 6 can be located on and in any portion of the therapeutic formulation 5. Preferably, the medicament 6 can be located on the entire skin contact side of the therapeutic formulation 5. When the adhesive skin patch 1 is placed upon the skin surface of a patient, the medicament 6 in this configuration will be in continuous contact with the skin surface of the patient.

The medicament 6 can relieve topical discomfort associated with a viral infection. As such, the adhesive patch 1 of the present invention can be applied to a clean and dry skin surface having a viral infection, thereby relieving the topical discomfort associated with the viral infection, such as pain, tingling, itching, and burning sensation.

Antimicrobial Agent

The therapeutic formulation 5 includes an antimicrobial agent 7 useful for preventing bacterial growth, mold growth, fermentation, and/or decomposition (i.e., preservative). As used herein, "antimicrobial agent" or "preservative" is any substance which prevents bacterial growth, mold growth, fermentation, and/or decomposition. *Concise Chemical and Technical Dictionary,* 4th enlarged edition, Chemical Publishing Co., Inc., N.Y., N.Y. p. 939 (1986). Any suitable antimicrobial agent 7 can be employed, provided the antimicrobial agent 7 effectively prevents bacterial growth, mold growth, fermentation, and/or decomposition and the antimicrobial agent 7 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1.

Suitable antimicrobial agent 7 include, e.g., quat-15 (also known as quaternium-15, Q-15, or methenamine 3-chloro-allylochloride) parabens, dichlorobenzyl alcohol, ethylene diamine tetreacetic acid, formaldehyde, gum benzoin, imidazolidinyl urea, phenyl-mercuric acetate, poly aminopropyl biguanide, propyl gallate, sorbic acid, cresol, chloroacetamide sodium benzoate, chloromethyl-methylisothiazolinone, chloromethyl-methylisothiazolon, chloromethyl-methylisothiazolinone benzalkonium chloride, an octylisothiazolinone benzimidazol-compound, chloromethyl-methylisothiazolinone octylisothiazolinone, o-phenylphenol benzisothiazolinone, o-phenylphenol benzisothiazolinone, benzisothiazolinone, an aliphatic amine of 2-thiopyridineoxide, benzoic acid, editic acid, phenolic acid, benzyl alcohol, isopropyl alcohol, benzenethonium chloride, bronopol, cetrimide, chlorohexidine, chlorobutanol, chlorocresol, phenol, phenoxyethanol, phenyl ethyl alcohol, phenylmercuric acetate, phenylmercuric borate, phenylmercuric nitrate, potassium sorbate, proplyene glycol, sodium benzoate, sodium propionate, thimerosol, and medicinally acceptable salts thereof. Preferably, the preservative is quat-15, which is commercially available from Dow Chemical (Midland Mich.); methyl paraben; ascorbic acid; or a combination thereof.

The antimicrobial agent 7 can be employed in any suitable amount provided the amount of antimicrobial agent 7 effectively prevents bacterial growth, mold growth, fermentation, and/or decomposition and the effective amount of antimicrobial agent 7 remains stable in the therapeutic formulation 5 over a prolonged period of time. Typically, the antimicrobial agent 7 can be present in about 0.01 wt. % to about 99.9 wt. % of the therapeutic formulation 5. The amount of antimicrobial agent 7 present in the therapeutic formulation 5 will typically depend upon the specific compound or compounds employed as the antimicrobial agent 7. For example, quat-15 can be employed in about 0.01 wt. % to about 1.5 wt. % of the therapeutic formulation 5, in about 0.05 wt. % to about 0.15 wt. % of the therapeutic formulation 5, or in about 0.08 wt. % to about 0.12 wt. % of the therapeutic formulation 5.

Solvent

The solvent 13 can act as a carrier for, and preferably can dissolve, the antiviral agent 15; the medicament 6; the antimicrobial agent 7; and/or the adhesive 14. Any suitable solvent 13 can be employed, provided the solvent 13 effectively dissolves the antiviral agent 15, the medicament 6, the antimicrobial agent 7, and/or the adhesive 14, and the solvent 13 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1.

The solvent 13 can include one or more organic compounds, one or more inorganic compounds, or mixtures thereof. Preferably, the solvent 13 will include one or more organic compounds, e.g., esters, terpenes, alcohols, ketones, aldehydes, fatty acids, partially or fully esterified fatty acids, wherein the structures are cyclic, non cylcic (e.g., alkyl), alicyclic (i.e., a bridged ring compound) or aromatic, as well as organic compounds having combinations of these functional groups. Suitable exemplary solvents 13 are disclosed, e.g., in Aldrich Handbook of Fine Chemicals, 2000-2001 (Milwaukee, Wis.). Specifically, the solvent 13 can include water (e.g., deionized water).

In one embodiment of the present invention, the solvent 13 can include a $(C_1-C_{12})$ acyclic hydrocarbon, a $(C_3-C_{12})$ cyclic hydrocarbon, a $(C_6-C_{12})$ aryl hydrocarbon, a $(C_6-C_{12})$ heteroaryl hydrocarbon, or a $(C_3-C_{12})$ heterocyclic hydrocarbon;

wherein any of the hydrocarbons can optionally include one or more carbon-carbon double bonds and any of the hydrocarbons can optionally include one or more carbon-carbon triple bonds;

wherein any of the hydrocarbons can optionally include one or more oxy (—O—), carbonyl (—C(=O)C—), carboxylato (—C(=O)O—), dioxy (—O—O—), dithio (—S—S—), imino (—NH—), methylene dioxy (—OCH$_2$O—), sulfinyl (—SO—), sulfonyl (—SO$_2$—), or thio (—S—);

wherein any of the hydrocarbons can optionally be substituted with one or more amino, hydroxyl, cyano, nitro, $(C_1-C_{12})$alkoxy, halo, trifluoro, trifluoro $(C_1-C_{12})$alkyl, NR$^1$R$^2$, or COOR$^1$; wherein R$^1$ and R$^2$ are each independently hydrogen, a $(C_1-C_{12})$ acyclic hydrocarbon or a $(C_3-C_{12})$ cyclic hydrocarbon.

The solvent 13 can be employed in any suitable amount, provided the amount of solvent 13 is effective to dissolve the antiviral agent 15, the medicament 6, the antimicrobial agent 7, and/or the adhesive 14 and the effective amount of solvent 13 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1.

In one embodiment, one or more fragrances 8 can be employed as a solvent 13. In another embodiment, one or more fragrances 8 can be employed in addition to the use of a solvent 13. As used herein, a "fragrance" is a compound that emits a sweet or pleasant odor or scent. *The American Heritage Dictionary of the English Language*, Houghton Mifflin Company, Boston, Mass., p. 521 (1981). The fragrance 8 can either at least partially mask the odor of the antiviral agent 15, if such an odor is present, or the fragrance 8 can provide a pleasant odor to the patch 1. Specifically, the pleasant odor can be a floral scent, a food scent, a fruit scent, a plant leaf scent, or any combination thereof. As such, the odor of the patch 1 is preferably pleasant to the patient, due to the odor or scent of the one or more fragrances.

A suitable fragrance 8 can be employed as a carrier (i.e., solvent) or co-carrier (i.e., co-solvent). The use of a fragrance 8 such as eucalyptus oil as a solvent 13 requires lower amounts of total solvent 13 to be used. Lower amounts of total solvent 13 allows for improved manufacturing characteristics. For example, if no fragrance 8 (e.g., eucalyptus oil) is employed as a solvent 13, about 8.0 wt. % propylene glycol is needed to dissolve the medicament 6 (e.g., camphor and lidocaine). The use of a suitable fragrance 8 (e.g., eucalyptus oil) requires only about 1.6 wt. % of the fragrance 8 and only about 2.0 wt. % of propylene glycol to be used to dissolve the medicament 6 (e.g., camphor and lidocaine). As such, less overall amounts of solvent 13 are required when a fragrance 8 such as eucalyptus oil is employed. The use of lower amounts of glycerin, ethylene glycol, and/or propylene glycol allows the adhesive patch 1 to be more effectively coated during the manufacturing process. Specifically, the use of lower amounts of propylene glycol results in less bleed-through or leak-through of the therapeutic formulation 5 onto the back side 4 of backing 2 in manufacturing of the adhesive patch 1. As such, the use of a suitable fragrance 8 as a solvent 13 can result in less bleed-through or leak-through of the therapeutic formulation 5 onto the back side 4 of backing 2 in manufacturing of the adhesive patch 1.

Preferably, the suitable fragrance 8 is a non-irritant to mammalian (e.g., human) skin. As used herein, "non-irritant" refers to an agent, e.g., organic compound, that does not produce an appreciable or significant amount of inflammation or irritation when applied topically to the skin of a mammal in the specified amount. As such, the fragrance 8 is preferably pharmaceutically acceptable for topical use.

It is preferred that the fragrance 8 have a low to moderate volatility, so that its evaporation from the patch 1 is rendered minimal to moderate. The volatility will, however, be high enough such that when desirable, the odor or scent can be detected by the patient. Preferably, the therapeutic formulation 5 of the adhesive patch 1 will emit an odor or scent, due to the fragrance 8, that is detected by the patient for a period of at least about 10 hours, at least about 8 hours, or at least about 6 hours.

Any suitable fragrance 8 can be employed, provided the fragrance 8 effectively dissolves the antiviral agent 15, the medicament 6, the antimicrobial agent 7, and/or the adhesive 14; the fragrance 8 remains stable in the therapeutic formulation 5; and the fragrance 8 either at least partially masks the odor of the antiviral agent 15, if such an odor is present, or provides a pleasant odor to the patch 1. Preferably, the stability is over a prolonged period of time, e.g., up to about 2 years, up to about 1 year, or up to about 6 months, typically experienced in the manufacturing, packaging, shipping, and/or storage of the patch 1. It is appreciated that the suitable fragrances would be known to those skilled in the art. It is also appreciated that those skilled in the art understand that suitable fragrances are commercially available from, for example, Alpine Aromatics (Piscataway, N.J.), Andrea Aromatics (Princeton, N.J.), Arylessence, Inc. (Marietta, Ga.), Belmay Co., Inc. (Yonkers, N.Y.), Crami Flavor & Fragrance Co., Inc. (City of Commerce, Calif.), Creative Fragrances Mfgr. Inc. (Dallas, Tex.), Drom International Co. (Tawaco, N.J.), Fleurchem, Inc. (Middletown, N.Y.), Great Lakes Chem. Corp. (Lafayette, Ind.), Kraus & Co., Inc. (Battle Creek, Mich.), The Lebermuth Co., Inc. (Mishawaka, Ind.), Penta Manufacturing (Livingston, N.J.), Shaw Mudge & Co. (Shelton, Conn.), Synarome Corp. (NY, N.Y.), Penreco (Houston, Tex.), Tracy Chemical Co. (Portland, Oreg.), Belle-Aire Fragrances (Mundelein, Ill.), Gusta Fragrances Co. (Chesire, Conn.), Atlanta Fragrance (Kennesaw, Ga.), and Bell Flavors & Fragrances, Inc (Northbrook, Ill.).

As the number of suitable fragrances is too voluminous and expansive to exhaustively list herein, suitable exemplary fragrances are disclosed herein. Suitable exemplary fragrances include grape fragrance, musk fragrance, light vanilla fragrance, Jergens lotion fragrance, Vaseline Intensive Care fragrance, Nivea Lotion fragrance, Ivory Soap fragrance, amaretto, blueberry, coffee, eggnog, peanut butter, rum cake, honey almond, ginger bread house, coffee cake & spice, raspberry rose, sassafras, strawberry, grapefruit pink, home sweet, jeweled citrus, lemon, mango, mulberry, orange flower, passion fruit, pikaki, freesia, china rain, coconut, apple, baked bread, cornucopia, lemon chiffon, peppermint twist, white cake, cherry pie, sugar plum, plum, romantic, sea fresh, tea, green floral, honeydew, kiwi, lilac, may bouquet, neutralizer, patchouli, peach, pine apple blossom, chocolate mint, frankincense, baked apple pie, cappuccino, cran-apple, maple syrup, popcorn (buttered), sugar cookie, cotton candy, cranberry cobbler, plumeria, rum, spring fever, watermelon, guava, honeysuckle, hyacinth, macadamia nut, melon, oakmoss, papaya, pear pineapple, blueberry, citrus-ginseng, garden dreams, banana creme pie, chocolate mint, cranberry, macadamia nut, pumpkin pie, chocolate German cake, banana nut bread, sweet potato pie, raspberry, sandalwood, spring flowers, ylang, heather, jasmine, lavender, magnolia, mountain air, orange essence, paradise, peony, alpine breeze, chamomile, clover, gardenia, or any combination thereof. Preferably, the fragrance 8 is eucalyptus oil.

Any suitable amount of fragrance 8 can be employed, provided the effective amount of fragrance 8 effectively dissolves the antiviral agent 15, the medicament 6, the antimicrobial agent 7, and/or the adhesive 14; the effective amount of fragrance 8 remains stable in the therapeutic formulation 5; and the effective amount of fragrance 8 either at least partially masks the odor of the antiviral agent 15, if such an odor is present, or provides a pleasant odor to the patch 1 over a prolonged period of time. Typically, the suitable amount of fragrance 8 will depend upon the specific fragrance 8 or fragrances 8 employed.

When the adhesive patch 1 of the present invention is used with patients having received a vaccination (e.g., cowpox vaccination), the solvent 13 can optionally not include an alcohol or any other substance that would kill or weaken a live vaccinia virus. Specifically, when the adhesive patch 1 of the present invention is used with patients having received a vaccination (e.g., cowpox vaccination), the solvent 13 can optionally not include ($C_1$-$C_{12}$)alkyl or ($C_3$-$C_{12}$) cycloalkyl substituted with one or more hydroxyl groups. More specifically, when the adhesive patch 1 of the present invention is used with patients having received a vaccination (e.g., cowpox vaccination), the solvent 13 can optionally not include isopropyl alcohol.

Essential Oil

As used herein, an "essential oil" 21 refers to a highly odoriferous, volatile liquid component obtained from plant tissue. Essential oils 21 typically include a mixture of one or more terpenes, esters, aldehydes, ketones, alcohols, phenols, and/or oxides. These functional classes of compounds are responsible for the therapeutic properties and distinct fragrance of the essential oil.

In one embodiment, the essential oil 21 is not: methyl salicylate, menthol, camphor, eucalyptus oil, spearmint oil, or a combination thereof.

In one embodiment of the present invention, the formulation 5 can include methyl salicylate, menthol, camphor, eucalyptus oil, spearmint oil, or a combination thereof. In such an embodiment, the formulation 5 can also include one or more essential oils 21 as defined herein.

In one embodiment of the present invention, the essential oil 21 is not: oil of wintergreen, thymol, oil of peppermint, spirits of turpentine, ephedra, coltsfoot, ginger, cinnamon oil, fir needle oil, lemon oil, Peruvian Balsam, or a combination thereof. Again, in such an embodiment, the formulation 5 of the present invention can include any one or more of oil of wintergreen, thymol, oil of peppermint, spirits of turpentine, ephedra, coltsfoot, ginger, cinnamon oil, fir needle oil, lemon oil, Peruvian Balsam, or a combination thereof; provided an essential oil 21 as defined herein is included in the formulation 5.

In one embodiment of the present invention, the formulation 5 can include oil of wintergreen, thymol, oil of peppermint, spirits of turpentine, ephedra, coltsfoot, ginger, cinnamon oil, fir needle oil, lemon oil, Peruvian Balsam, or a combination thereof. In such an embodiment, the formulation 5 will also include one or more essential oils 21 as defined herein.

The essential oil 21 can be manufactured (i.e., synthesized or partially synthesized). Alternatively, the essential oil 21 can be obtained from a plant or plant component (e.g., plant tissue). Suitable plant or plant components include, e.g., a herb, flower, fruit, seed, bark, stem, root, needle, bulb, berry, rhizome, rootstock, leaf, or a combination thereof.

Any suitable essential oil 21 can be employed provided (1) the essential oil 21 has therapeutic properties (e.g., the essential oil 21 effectively relieves discomfort), (2) the essential oil 21 provides a scent that is associated with plant tissue, and/or (3) the essential oil 21 remains stable in the formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. The specific essential oil 21 will preferably be non-toxic to mammals (e.g., humans) and will be suitable for medicinal use (e.g., topically or via inhalation). The specific essential oil 21 will also preferably comply with any controlling or governing body of law, e.g., FDA regulations.

Suitable specific essential oils 21 include, e.g., one or more of the following: ajowan, sweet almond oil, allspice, aloe vera oil, ammi visnaga (khella), amyris, angelica root, angelica seed, anise, anise seed, star anise, apricot kernel oil, absolute arnica, avocado oil, unrefined avocado oil, Copaiba balsam, balsam Peru genuine, balsam Peru oil, balsam peru liquid resin, balsam tolu, sweet french basil, basil, basil ct. methyl chavicol, lemon ct. citral basil, sweet ct. linalool basil, bay laurel, bay leaf, bay rum, bay leaf West Indies, bees wax, unrefined bees wax, benzoin absolute, benzoin resinoid, bergamot, mint bergamot, Italian bergamot oil, free bergaptene bergamot, birch, sweet birch, borage oil, boronia, butter, buchu leaf, cajeput, calamus, calendula oil, infused calendula oil, camellia oil, cannabis, caraway, caraway seed, cardamom, absolute carnation, carrot seed, high carotol carrot seed, carrot seed oil, cassia, cassis bud (black currant), castor oil, catnip, oil of catnip, cedarleaf, western red cedarleaf, cedarwood, Atlas cedarwood, Himalayan cedarwood, Virginia cedarwood, celery seed, chamomile, blue chamomile, German chamomile, Moroccan chamomile, Moroccan wild chamomile, Roman chamomile, champaca, cilantro, true cinnamon bark, cinnamon bark, cinnamon leaf, cinnamon cassia, cistus, citronella, Java citronella, ciste oil, artificial civet, clary sage, high sclareol clary sage, clementine, Italian clementine peel oil, clove, clove bud, clove leaf, cocoa, cocoa butter, unrefined cocoa butter, coconut oil, refined coconut oil, cognac, combava petitgrain, coriander, green coriander, cornmint, costus oil, cumin, cypress, davana oil, dill, dill weed, elemi, erigeron (fleabane), eucalyptus citriodora, eucalyptus globulus, lemon eucalyptus, fennel, sweet fennel, fenugreek, fir, Canada fir needle, Siberia fir needle, white fir needle, frankincense, India frankincense, Oman frankincense, galbanum oil, garlic, genet, geranium, geranium leaf, geranium rose, Bourbon geranium, Egyptian geranium, ginger, Cochin extra ginger, ginsing, Siberian ginsing, Korean ginsing, grapefruit, pink grapefruit, white grapefruit, grapeseed oil, hazelnut oil, helichrysum, helichrysum immortelle, Mad. helichrysum, Balkan helichrysum, Corsica helichrysum, France helichrysum, hemp oil, absolute honeysuckle, hyssop, hyssop decumbens, absolute immortelle, fragrant aster inula, Jamaican gold, unrefined Jamaican gold, jasmine, absolute jasmine, grandiflorum jasmine, sambac jasmine, jojoba oil, helio-carrot in jojoba, melissa in jojoba, absolute jonquille, juniper berry, Siberia juniper berry, Croatia juniper berry, lanolin, unrefined anhydrous lanolin, lantana camara, laurel nobilis, lavandin, abrialis lavandin, grosso lavandin, lavender, Oregon lavender, Bulgarian lavender, Russian lavender, high-altitude lavendar, wild-crafted lavender, lavendin, organic lavindin, lemon, lemongrass, lime, distilled lime, expressed lime, litsea, litsea cubeba, blue, pink and white lotus, macadamia oil, mace, green mandarin, red mandarin, yellow mandarin, manuka, absolute marigold, marigold flower, marjoram, Spanish marjoram, sweet marjoram (true), massoia bark, melissa, codistilled melissa, "rectified" melissa, true melissa, absolute mimosa, mimosa, monarda, mugwort, musk seed, myrrh, myrtle, absolute narcissus, neroli (orange blossom), niaouli, nutmeg, extra nutmeg, oakmoss, absolute oak moss, olibanum, absolute opopanax, bitter orange, blood orange, sweet orange, wild West Indian orange, oregano, orris root, concrete orris, osmanthus, palm oil, refined palm oil, palmarosa, paprika, parsley seed, patchouli, Indian patchouli oil, Indonesian patchouli oil, peanut, peanut oil, pecan oil, pennyroyal, pepper, black pepper, super black pepper, peppermint, India peppermint, USA baby mint peppermint, pet perfume, petitgrain (orange leaves), white pine, pine needle, evening primrose, ravensara anisata, true ravensara, ravensare, ravintsara, redberry, rosalina, rose, rose geranium, rose otto, Bulgarian rose, English rose, Turkish rose, rosehip seed oil, rosemary, rosemary anti-oxidant extract powder, rosemary verbenone, Morocco rosemary, Spain rosemary, rosewood, rosewood oil, rue, sage, white sage, sage dalmatian, sage officinalis, sage triloba, sandalwood, seabuckthorn berry, sesame oil, sesame seed oil, shea butter, unrefined shea butter, spikenard, green spikenard, spruce, St. John's wort, styrax resin, tagetes, tangerine, Dancy tangerine, tarragon, tea tree, Australia tea tree, thuja (cedar leaf), thyme, red thyme, thyme ct. linalool, thyme vulgaris, wild thyme, red thyme, mixed tocopherols, tolu balsam resin, absolute tuberose, tuberose, tumeric, valerian, vanilla, pure vanilla extract, vanilla bean, absolute vanilla bourbon, vegetable glycerin, absolute verbena, vetiver, violete leaves, vitex, organic Haiti vetiver, absolute violet leaf, walnut oil, wintergreen, natural wintergreen, wormwood, yarrow, ylang ylang, ylang ylang I, ylang ylang II, ylang ylang III, ylang ylang compound, ylang ylang complete, and ylang ylang extra.

Specifically, suitable exemplary essential oils 21 include, e.g., angelica root, anise, basil (e.g., sweet French basil), bay leaf, benzoin absolute, bergamot, birch, carrot seed, cedarwood, chamomile (e.g., German chamomile, Moroccan chamomile, or Roman chamomile), cinnamon leaf, cinnamon *cassia*, cistus, citronella, clary sage, clove bud, cypress, eucalyptus globulus, eucalyptus citriodora, everlasting (helicrysum), fennel, fir, frankincense, geranium, ginger, grapefruit, *helichrysum*, hyssop, juniper berry, lavender, lavendin, lemon, lemongrass, lime, marjoram, myrrh, myrtle, neroli, niaouli, nutmeg, sweet orange, oregano, patchouli, pennyroyal, peppermint, petitgrain, pepper, pine needle, ravensare, rose geranium, rosemary (e.g., Spanish rosemary), rosewood, sage, sandalwood, spikenard, spruce, tangerine, tarragon, tea tree, thyme, vanilla, vetiver, ylang ylang, or a combination thereof.

Other suitable essential oils 21 that can be employed in the adhesive skin patch 1 of the present invention are disclosed in the accompanying documents herein, which form part of this provisional patent application. Other suitable essential oils 21 that can be employed in the adhesive skin patch 1 of the present invention are disclosed in the following websites: www.essential-essences.com; www.fragrancefactory.com; www.essentialoil.com; www.essentialoils.org; www.halcyon.com; and www.essential-oil.org; which are all incorporated by reference herein.

The essential oil 21 can be present in any appropriate and suitable amount, provided (1) the amount of essential oil 21 has therapeutic properties (e.g., the amount of essential oil 21 effectively relieves discomfort), (2) the amount of essential oil 21 provides a scent that is associated with plant tissue, and/or (3) the amount of essential oil 21 remains stable in the formulation 5. Preferably, the stability is over a prolonged period of time, e.g., up to about 3 years, up to about 1 year, or up to about 6 months, typically experienced in the manufacturing, packaging, shipping, and/or storage of the adhesive skin patch 1. The specific amount of essential oil 21 will preferably be non-toxic to mammals (e.g., humans) and will be suitable for medicinal use (e.g., topically or via inhalation). The specific amount of essential oil 21 will also preferably comply with any controlling or governing body of law, e.g., FDA regulations.

Typically, the amount of essential oil 21 present in the formulation 5 will depend upon the specific compound or compounds employed as the essential oil 21. Specifically, the essential oil 21 can be present in about 0.01 wt. % to about 99.9 wt. % of the formulation 5. More specifically, the essential oil 21 can be present up to about 50 wt. % of the formulation 5, up to about 25 wt. % of the formulation 5, up to about 20 wt. % of the formulation 5, up to about 10 wt. % of the formulation 5, or up to about 5 wt. % of the formulation 5.

In one embodiment of the present invention, angelica root, anise, basil (e.g., sweet French basil), bay leaf, benzoin absolute, bergamot, birch, carrot seed, cedarwood, chamomile (e.g., German chamomile, Moroccan chamomile, or Roman chamomile), cinnamon leaf, cinnamon cassia, cistus, citronella, clary sage, clove bud, cypress, eucalyptus globulus, eucalyptus citriodora, everlasting (helicrysum), fennel, fir, frankincense, geranium, ginger, grapefruit, helichrysum, hyssop, juniper berry, lavender, lavendin, lemon, lemongrass, lime, marjoram, myrrh, myrtle, neroli, niaouli, nutmeg, sweet orange, oregano, patchouli, pennyroyal, peppermint, petitgrain, pepper, pine needle, ravensare, rose geranium, rosemary (e.g., Spanish rosemary), rosewood, sage, sandalwood, spikenard, spruce, tangerine, tarragon, tea tree, thyme, vanilla, vetiver, ylang ylang, or a combination thereof, or any combination thereof, can be present up to about 20 wt. % of the formulation, up to about 10 wt. % of the formulation, or up to about 5 wt. % of the formulation.

The adhesive skin patch 1 includes an essential oil 21 located in at least a portion of the front side 3 of the backing 2, on at least a portion of the front side 3 of the backing 2, or on and in at least a portion of the front side 3 of the backing 2. As such, the essential oil 21 can be located on the entire surface of the front side 3 of the backing 2 or the essential oil 21 can be located on a portion of the surface of the front side 3 of the backing 2. Preferably, the essential oil 21 can be located on the entire surface of the front side 3 of the backing 2.

In addition to being located on the surface of the front side 3 of the backing 2, the essential oil 21 can be located in at least a portion of the underlying surface of the front side 3 of the backing 2 (i.e., the essential oil 21 can be partially embedded into the backing 2). As shown in FIG. 9, the essential oil 21 can penetrate a substantial portion of the front side 3 of the backing 2, as disclosed, e.g., in U.S. Pat. No. 5,536,263, and references cited therein. For example, the essential oil 21 can penetrate about one-tenth to about nine-tenths the thickness of the backing 2, or about one-fourth to about nine-tenths the thickness of the backing 2. As such, the essential oil 21 can be partially embedded into the backing 2.

Preferably, the essential oil 21 can be located on the entire front side 3 of the backing 2 and partially in the front side 3 of the backing 2 (i.e., the essential oil 21 is partially embedded into the backing 2). Alternatively, a portion of the front side 3 of the backing 2 can include the essential oil 21 and other portions of the front side 3 of the backing 2 can include the pressure sensitive adhesive. For example, a central circular portion of the front side 3 of the backing 2 can include the essential oil 21 while the remaining portions of the front side 3 of the backing 2 include only the pressure sensitive adhesive 14. When the adhesive skin patch 1 is placed upon the skin of a patient (e.g., human), the essential oil 21 can be in continuous contact with the skin surface of the patient.

Plant Tissue

The essential oil 21 can be derived from plant tissue.

As used herein, "plant tissue" refers to the tissue of any organism of the plant kingdom, as opposed to one of the animal kingdom or of the kingdoms of Fungi, Protista, or Monera. The plant tissue can be any portion or portions of the plant (e.g., bark, roots, leaves, flowers, needles, bulbs, berries, rhizomes, rootstocks, stems, and seeds), as well as the entire plant. The tissues of a plant ("plant tissue") generally fall into three main categories: dermal tissue, ground tissue, and vascular tissue. Dermal tissue refers to the "skin" layer of all plant organs and is responsible for environmental interaction (light passage, gas exchange, pathogen recognition and protection, color display, etc.).

Dermal tissue is composed of epidermal cells, closely packed cells that secrete a waxy cuticle that aids in the prevention of water loss. Ground tissue lies between dermal tissue and vascular tissue. The ground tissue comprises the bulk of the primary plant body. Parenchyma, collenchyma, and sclerenchyma cells are common in the ground tissue. In roots, the ground tissue may store sugars or starches to fuel the spring sap flow; in leaves, the ground tissue is the layer responsible for photosynthesis (the mesophyll). Vascular tissue transports food, water, hormones and minerals within the plant. Vascular tissue includes xylem, phloem, parenchyma, and cambium cells.

As used herein, "bark" refers to the dry, dead outer covering of woody branches, stems and roots of plants that is very distinct and separable from the wood itself. It includes all tissue outside the cambium (growth layer between bark and wood).

As used here the terms "leaf" or "leaves" refer to those parts of a plant which grow along the sides of branches or stems or at the bases of plants. Most are green and contain chlorophyll, though they vary in their shapes and sizes. Leaves are the part of the plant that ordinarily performs photosynthesis (the process that converts sunlight and carbon dioxide into energy).

As used herein, "needle" generally refers to a narrow stiff leaf, such as those of conifers (e.g., pine trees).

As used herein, "root" refers to the part of a plant, normally underground, that absorbs nutrients and anchors the plant into the ground.

As used herein, "bulb" refers to a spheroidal body growing from a plant either above or below the ground (usually below), which is usually a bud, consisting of a cluster of partially developed leaves, and producing, as it grows, a stem above, and roots below, (e.g., the onion or tulip bulb). A true bulb is a complete package containing next year's plant (flower) already forming inside. The contents of the bulb are often enclosed in protective, fleshy scales, which are held together by a small basal plate. The scales are modified leaves that contain enough nutrients to sustain the plant through dormancy and early growth. They may be loose and open like those of a lily, or tightly closed like those of a hyacinth. In many bulbs, a paper-thin tunic protects the scales (lilies don't have a tunic). Roots will grow from the bulb's basal plate.

As used herein, "berry" refers to any small fruit that is pulpy or succulent throughout, having seeds loosely imbedded in the pulp, such as the currant, grape, or blueberry. Berry can be further defined as an indehiscent fruit derived from a single ovary and having the whole wall fleshy, such as the grape or tomato. Furthermore, berries come in various structures including simple, such as grape; blueberry, cranberry, or aggregate, such as blackberry; raspberry, strawberry mulberry.

As used herein, "rhizome" refers to a horizontal, usually underground stem that often sends out roots and shoots from its nodes (also called rootstalk or rootstock).

As used herein, "rootstock" refers to a robust plant that provides the root system in grafting, also known as a stock. Scions and buds are grafted and budded to a rootstock or stock. Rootstock also refers to the elongated and often thick rhizomes of certain perennial herbaceous plants such as the Iris, Aspidistra and Solomon's Seal.

As used herein, "stem" refers to the main (usually aerial) axis (sometimes referred to as the trunk or stalk) of a tree, shrub, or plant. "Stem" also refers to the part of the plant that supports the leaves, flowers or fruits of a plant, such as the peduncle of a fruit or the pedicel of a flower.

As used herein, "seed" refers to a ripened ovule, consisting of an embryo with one or more integuments, or coverings, such as an apple seed, a currant seed, dill seed, or kola nut seed. By germination, most seeds produce a new plant. "Seed" also refers to any small seedlike fruit, though it may consist of a pericarp, or even a calyx, as well as the seed proper, such as a parsnip seed or thistle seed. The seed proper has an outer and an inner coat, and within these the kernel or nucleus. The kernel is either the embryo alone, or the embryo enclosed in the albumen, which is the material for the nourishment of the developing embryo. The scar on a seed, left where the stem parted from it, is called the hilum, and the closed orifice of the ovule, the micropyle.

Preferably, the solvent 13 can be a fragrance 8 that can either at least partially mask the odor of the antiviral agent 15, the medicament useful for treating topical discomfort 6, and/or the antimicrobial agent useful for preventing bacterial growth, mold growth, fermentation, and/or decomposition 7, if such odor is present; or can provide a pleasant odor to the patch 1.

Adhesive

Any suitable adhesive 14 can be employed, provided the adhesive 14 provides the requisite adhesiveness to the patch 1 and the adhesive 14 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. It is appreciated that the suitable adhesives would be known to those skilled in the art. Suitable adhesives are disclosed, e.g., in U.S. Pat. No. 4,675,009; U.S. Pat. No. 5,536,263; U.S. Pat. No. 4,696,854; U.S. Pat. No. 5,741,510, and references cited therein. Preferably the adhesive 14 is an acrylic ester copolymer. Any suitable amount of adhesive 14 can be employed, provided the amount of adhesive 14 effectively provides the requisite adhesiveness to the patch 1 and the effective amount of the adhesive 14 remains stable in the therapeutic formulation 5 over a prolonged period of time. Typically, the suitable amount of adhesive 14 will depend upon the specific adhesive 14 or adhesives 14 employed. Typically, the therapeutic formulation 5 can include an adhesive 14 in about 0.1 wt. % to about 50 wt. % of the therapeutic formulation 5. Preferably, the therapeutic formulation 5 can include an adhesive 14 in about 0.5 wt. % to about 10.0 wt. % of the therapeutic formulation 5. More preferably, the therapeutic formulation 5 can include an adhesive 14 in about 1.0 wt. % to about 15.0 wt. % of the therapeutic formulation 5.

Alternatively, the adhesive 14 can include a hot melt pressure sensitive adhesive or solvent based pressure sensitive adhesive (e.g., polyacrylate, polyisobutylene, and polybutene), rubber, silicone based pressure sensitive adhesives (e.g., polydimethylsiloxane and resin mixtures), polystyrene-polybutadiene-polystyrene, polystyrene-polyisoprene-polystyrene, polystyrene-poly(ethylene-butylene)-polystyrene block polymers, or any combination thereof. In addition, the adhesive 14 can include a resin emulsion adhesive, wherein the resin emulsion adhesive can include vinyl acetate resin, acrylic ester copolymer, vinyl actetate/diocyl maleate copolymer, acrylic copolymer, or any combination thereof.

Other suitable adhesives 14 are disclosed, e.g., in U.S. Pat. No. 4,675,009; U.S. Pat. No. 5,536,263; U.S. Pat. No. 4,696,854; U.S. Pat. No. 5,741,510, and references cited therein.

The adhesive 14 can be located on and in any portion of the therapeutic formulation 5. Preferably, the adhesive 14 can be located on the entire skin contact side of the therapeutic formulation 5. When the adhesive skin patch 1 is placed upon the skin surface of a patient, the adhesive 14 in this configuration is in continuous contact with the skin surface of the patient.

Polymers

The therapeutic formulation 5 can optionally include one or more polymers 9. The polymer 9 provides structure and strength to the adhesive 14. Any suitable polymer 9 can be employed, provided the polymer 9 provides structure and strength to the adhesive 14 and the polymer 9 remains stable the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. Suitable polymers 9s include, e.g., starch, starch derivatives, polyvinyl pyrrolidone, polyethylene oxide, polyacrylate quats, polymaleic acid, polymaleic anhydride, polyurethanes, polyureas, karaya, gum acacia, locust bean gum, xanthan gum, guar gum, modified guar gum, maltodextrin, carboxymethyl cellulose, carboxypropyl cellulose, polyacrylamide, polyvinyl alcohol, poly AMPS, and polyacrylates. Other suitable polymers 9 are disclosed, e.g., in U.S. Pat. No. 4,675,009; U.S. Pat. No. 5,536,263; U.S. Pat. No. 4,696,854; U.S. Pat. No. 5,741,510, and references cited therein. Preferably, the polymer 9 is karaya.

Any suitable amount of polymer 9 can be employed, provided the amount of polymer 9 effectively provides structure and strength to the adhesive 14 and the effective amount of polymer 9 remains stable the therapeutic formulation 5 over a prolonged period of time. Typically, the suitable amount of polymer 9 will depend upon the specific polymer 9 or polymers 9 employed. For example, karaya can be employed as the polymer 9 in about 10 wt % to about 55 wt. % of the therapeutic formulation 5, in about 20 wt % to about 35 wt. % of the therapeutic formulation 5, or in about 23 wt % to about 29 wt. % of the therapeutic formulation 5. Preferably, karaya can be employed as the polymer 9 in about 24 wt % to about 28 wt. % of the therapeutic formulation 5.

Antibiotic Agent

The therapeutic formulation 5 can optionally include one or more suitable antibiotic agents. As used herein, an "antibiotic agent" is any compound having activity against either Gram-positive or Gram-negative organisms (i.e., inhibits the growth or destroys the development of either Gram-positive or Gram-negative organisms). *Stedman's Medical Dictionary, Illustrated*, (25th Ed.), Williams & Wilkins: Baltimore (1990) and *Mosby's Medical, Nursing, & Allied Health Dictionary*, (5th Ed.), Mosby: St. Louis (1998).

Any suitable antibiotic agent 16 can be employed, provided the antibiotic agent 16 effectively inhibits the growth or destroys the development of either Gram-positive or Gram-negative organisms and the antibiotic agent 16 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. Suitable antibiotic agents 16 are disclosed, e.g., in *Physician's Desk Reference (PDR)*, Medical Economics Company (Montvale, N.J.), (53rd Ed.), 1999; *Mayo Medical Center Formulary, Unabridged Version*, Mayo Clinic (Rochester, Minn.), January 1998; *Merck Index, An Encyclopedia of Chemicals, Drugs, and Biologicals*, (11th Ed.), Merck & Co., Inc. (Rahway, N.J.), 1989; *University of Wisconsin Antimicrobial Use Guide*, http://www.medsch.wisc.edu/clinsci/amcg/amcg.html; *Introduction on the Use of the Antibiotics Guideline, Descriptions of Specific Antibiotic Classes*, Thomas Jefferson University, http://jeffline.tju.edu/CWIS/OAC/antibiotics_guide/intro.html; and references cited therein. The antibiotic agent 16 is useful in preventing and/or treating secondary infections that are typically encountered with viral infections.

Suitable antibiotic agents 16 include, e.g., cilastatin, clavulanic acid, folinic acid, probenecid, pyridoxine, sulbactam, dapsone, ethambutol, isoniazid, pyrazinamide, rifampin, streptomycin, capreomycin, ethionamide, para aminosalicylic acid, cycloserine, ciprofloxacin, nalidixic acid, norfloxacin, ofloxacin, imipenam, meropenem, cilistatin, cefadroxil, cefazolin, cephalexin, cephalothin, cefaclor, cefamandole, cefonicid, cefoxitin, cefuroxine, cefoperazone, cefotaxime, ceftazidime, ceftazidime, ceftizoxime, ceftriaxone, moxalactam, cefepine, bacitracin, vancomycin, aztreonam, amoxicillin, clavulanic acid, benzathine, penicillin g, penicillin v, ampicillin, carbenicillin indamyl, carbenicillin, mezlocillin, piperacillin, ticarcillin, cloxacillin, dicloxacillin, floxacillin, methicillin, nafcillin, oxacillin, colistmethate, polymixin b, trimethoprim, co-trimoxazole, mafenide, sulfadiazine, sodium sulfacetamide, sulfacytine, sulfadiazine, sulfamethoxazole, sulfapyridine, sulfasalazine, sulfisoxazole, chloramphenicol, clindamycin, spectinomycin, azithromycin, clarithromycin, erythrmoycin, erythromycin estolate, spiramycin, chlortetracycline, demeclocycline, doxycycline, minocycline, oxytetracycline, amikacin, kanamycin, neomycin, streptomycin, tobramycin, nitrofurantoin, griseofulvin, potassium iodide, fluconazole, itraconazole, ketoconazole, miconazole, clotrimazole, amphotericin b, nystatin, niclosamide, nifurtimox, piperazine, praziquantel, pyrantel pamoate, ascariasis, thiabendazole, amodiaquine, chloroquine, hydroxychloroquine, mefloquine, primaquine, pyrimethamine, quinidine gluconate, fansidar, diloxanide furoate, melarsoprol, nifurtimox, paromomycin, pentamidine, sodium stibogluconate, suramin, metronidazole, foscamet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, foscamet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, and pharmaceutically acceptable salts thereof.

Any suitable amount of antibiotic agent 16 can be employed, provided the amount of antibiotic agent 16 employed effectively inhibits the growth or destroys the development of either Gram-positive or Gram-negative organisms and the effective amount of the antibiotic agent 16 remains stable in the therapeutic formulation 5 over a prolonged period of time. Typically, the amount of antibiotic agent 16 will depend upon the specific antibiotic agent 16 or agents employed. Typically, the antibiotic agent 7 can be present up to about 99.9 wt. % of the therapeutic formulation 5, up to about 50 wt. % of the therapeutic formulation 5, up to about 25 wt. % of the therapeutic formulation 5, or up to about 10 wt. % of the therapeutic formulation 5. Preferably, the antibiotic agent 7 can be present up to about 5.0 wt. % of the therapeutic formulation 5, up to about 1.0 wt. % of the therapeutic formulation 5, or up to about 0.5 wt. % of the therapeutic formulation 5.

Humectant

The therapeutic formulation 5 can optionally include one or more humectants 17 to provide a moistening effect to the adhesive 14. For example, the humectant 17 can hydrate the polymer 9. Any suitable humectant 17 can be employed, provided the humectant 17 effectively provides a moistening effect to the adhesive 14 and the humectant 17 remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. One suitable humectant 17 is glycerin. Other suitable humectants 17 s include polyhydric alcohols such as ethylene glycol, propylene glycol, triethylene glycol, tetraethylene glycol, and sorbitol.

Any suitable amount of humectant 17 can be employed, provided the amount of humectant 17 effectively provides a moistening effect to the adhesive 14 and the effective amount of humectant 17 remains stable in the therapeutic formulation 5. Typically, the suitable amount of humectant 17 will depend upon the specific humectant 17 or humectants 17 employed and the specific polymer 9 or polymers 9 employed. For example, karaya can be employed as the polymer 9 and glycerin can be employed as the humectant 17 in about 20 wt % to about 70 wt. % of the therapeutic formulation 5, preferably about 30 wt % to about 60 wt. % of the therapeutic formulation 5, or more preferably in about 40 wt % to about 50 wt. % of the therapeutic formulation 5.

Topical Moisturizer

The therapeutic formulation 5 can optionally include a topical moisturizer 18 (i.e., skin protectant). Any suitable topical skin protectant can be employed, provided the skin is effectively protected or moisturized and the skin protectant remains stable in the therapeutic formulation 5. Preferably, the stability is over a prolonged period of time, e.g., up to about 2 years, up to about 1 year, or up to about 6 months, typically experienced in the manufacturing, packaging, shipping, and/or storage of the patch 1. Suitable skin protectants include, e.g. aloe, lanolin, glycerin, calamine, Vitamin E, Vitamin E acetate, Vitamin C, allantoin, aluminum hydroxide gel, bismuth subnitrate, boric acid, calamine, cocoa butter, dimethicone, glycerin, kaolin, live yeast cell derivative, petrolatum, pyridoxine hydrochloride, shark liver oil, sodium bicarbonate, sulfur, tannic acid, topical starch, trolamine, white petrolatum, zinc acetate, zinc carbonate zinc oxide, zinc sulfate, shea butter, and any combination thereof.

As used herein, "calamine" is a pink powder of zinc oxide and a skin protectant containing about 98% zinc oxide and about 0.5% ferric oxide; "aloe" is the dried latex of leaves of Curaco Aloe (*Aloe barbadenis* Miller, Aloe vera Linne) or Cape Aloe (*Aloe ferox* Miller and hybrids), of the family *Liliacaea*; "Vitamin E" is 3,4-dihydro-2,5,7,8-tetramethyl-2-(4,8,12-trimethyltridecyl)-2H-1-benzopyran-6-ol; "Vitamin E acetate" is 3,4-dihydro-2,5,7,8-tetramethyl-2-(4,8,12-trimethyltridecyl)-2H-1-benzopyran-6-ol acetate; and "lanolin" is the fat-like secretion of the sebaceous glands of sheep (i.e., complex mixture of esters and polyesters of 33 high molecular weight alcohols and 36 fatty acids) which is deposited onto the wool fibers. Preferably, the topical moisturizer 18 can be aloe and Vitamin E.

Aloe is commercially available as Aloe Vera Gel from Terry Laboratories (Melbourne, Fla.). Aloe Vera Gel is commercially available as Aloe Vera Gel 40× (20.0 wt. % solution in water), Aloe Vera Gel 1× (0.5 wt. % solution in water), Aloe Vera Gel 10× (5.0 wt. % solution in water), or solid Aloe Vera. The solid Aloe Vera can be dissolved in a carrier, such as water, to the desired concentration. In addition, the commercially available forms of Aloe Vera are optionally available as decolorized Aloe Vera.

Any suitable amount of topical moisturizer 18 can be employed, provided the suitable amount of skin protectant effectively protects or moisturizes the skin and the effective amount of skin protectant remains stable in the therapeutic formulation 5 over a prolonged period of time. The suitable and effective amount of topical moisturizer 18 will depend in part upon the specific moisturizer 18 or moisturizers 18 present in the therapeutic formulation 5. For example, Aloe Vera Gel, 10× can be present up to about 40.0 wt. % of the therapeutic formulation 5. Preferably, Aloe Vera Gel, 10× can be present up to about 5.0 wt. % of the therapeutic formulation 5. More preferably, Aloe Vera Gel, 10× can be present up to about 1.0 wt. % of the therapeutic formulation 5. In addition, Vitamin E acetate can be present up to about 5 wt. % of the therapeutic formulation 5. Preferably, Vitamin E acetate can be present up to about 1.0 wt. % of the therapeutic formulation 5. More preferably, Vitamin E acetate can be present up to about 0.5 wt. % of the therapeutic formulation 5.

Polyhydric Alcohol

The therapeutic formulation 5 can optionally include one or more polyhydric alcohols 22. Suitable polyhydric alcohols 22 include, e.g., ethylene glycol, propylene glycol, triethylene glycol, tetraethylene glycol, sorbitol, or any combination thereof. Specifically, the polyhydric alcohol 22 can include propylene glycol.

Any suitable amount of polyhydric alcohol 22 can be employed. For example, the polyhydric alcohol 22 can be present up to about 35 wt. % of the therapeutic formulation 5, up to about 15 wt. % of the therapeutic formulation 5, or up to about 5 wt. % of the therapeutic formulation 5. Specifically, the polyhydric alcohol 22 can be present in about 0.5 wt. % to about 5.0 wt. % of the therapeutic formulation 5.

Water

The therapeutic formulation 5 can optionally include water, e.g., deionized water (DI). Any suitable amount of water can be employed, provided the amount of water maintains the adhesiveness of the adhesive 14 and maintains the appropriate stability of the therapeutic formulation 5. For example, deionized water can be present up to about 50 wt. % of the therapeutic formulation 5, up to about 40.0 wt. % of the therapeutic formulation 5, or up to about 30.0 wt. % of the therapeutic formulation 5. Specifically, deionized water can be present up to about 20.0 wt. % of the therapeutic formulation 5. More specifically, deionized water can be present up to about 10.0 wt. % of the therapeutic formulation 5. More specifically, deionized water can be present in about 5.0 wt. % to about 15.0 wt. % of the therapeutic formulation 5.

Anti-Fungal Agent

The therapeutic formulation 5 can optionally include one or more anti-fungal agents 23. Suitable anti-fungal agents 23 include, e.g.,

[1R-(1R*, 3S*, 5R*, 6R*, 9R*, 11R*, 15S*, 16R*, 17R*, 18S*, 19E, 21E, 23E, 25E, 27E, 29E, 31E, 33R*, 35S*, 36R*, 37S*)]-33-[(3-Amino-3,6-dideoxy-β-D-mannopyranosyl)oxy]-1,3,5,6,9,11,17,37-octahydroxy-15,16,18-trimethyl-13-oxo-14,39-dioxabicyclo[33.3.1]nonatriaconta-19,21,23,25,27,29,31-heptaene-36-carboxylic acid (Amphotericin B);

5-fluorocytosine (Flucytosine);
2,4-difluoro-α,α¹-bis(1H-1,2,4-triazol-1-ylmethyl) benzyl alcohol) (Fluconazole);
griseofulvin microsize (Griseofulvin);
(E)-N-(6,6-dimethyl-2-hepten-4-ynyl)-N-methyl-1-naphthalenemethanamine hydrochloride) (Terbinafine);
cis-1-acetyl-4-[4-[(2-(2,4-dichlorophenyl)-2-(1H-imadazol-1-ylmethyl)-1,3-dioxolan-4-yl]methoxyl]phenyl] piperazine (Ketoconazole);
(±)-1-[(R*)-sec-butyl]-4-[p-[4-[p-[[(2R*,4S*)-2-(2,4-dichlorophenyl)-2-(1H-1,2,4-triazol-1-ylmethyl)-1,3-dioxolan-4-yl]methyoxy]phenyl]-1-piperazinyl]phenyl]-Δ²-1,2,4-triazolin-5-one mixture with (±)-1-[(R*)-sec-butyl]-4-[p-[4-[p-[[(2S*, 4R*)-2-(2,4-dichlorophenyl)-2-(1H-1,2,4-triazol-1-ylmethyl)-1,3-dioxolan-4-yl]methoxy]phenyl]-1-piperazinyl]phenyl]-Δ²-1,2,4-triazolin-5-one or (±)-1-[(RS)-sec-butyl]-4-[p-[4-[p-[[(2R,4S)-2-(2,4-dichlorophenyl)-2-(1H-1,2,4-triazol-1-ylmethyl)-1,3-dioxolan-4-yl]-methoxy]phenyl]-1-piperazinyl]phenyl]-Δ²-1,2,4-triazolin-5-one (Itraconazole);
2-chloro-5-hydroxy-1,3-dimethylbenzene (Chloroxylenol);
griseofulvin ultramicrosize (Griseofulvin);
(E)-N-(6,6,-dimethyl-2-hepten-4-ynyl)-N-methyl-1-naphthalenemanamine hydrochloride (Terbinafine);
6-cyclohexyl-1-hydroxy-4-methyl-2(1H)-pyridinone (Ciclopirox);
N-4-tert-butyl-benzyl-N-methyl-1-naphthalenemethylamine hydrochloride (Butenafine hydrochloride);
nystatin;
(E)-N-(Cinnamyl-N-methyl-1-naphthalenemethylamine hydrochloride (Naftifine hydrochloride);
1-(2,4-dichlorophenyl)-2-(1H-imidazol-1-yl)—O—[(2,4-dichlorophenyl)methyl]oxime, (Z)—, mononitrate (Oxiconazole nitrate),
6-cyclohexyl-1-hydroxy-4-methyl-2(1H)-pyridone (Ciclopirox);
selenium sulfide;
(±)-1-[4-(p-chlorophenyl)-2-[(2,6-dichlorophenyl)thio]butyl] imidazole mononitrate (Butoconazole nitrate);
1-(o-Chloro-α, α-diphenylbenzyl)imidazole (Clotrimazole);
(cis-1-[p-[[2-(2,4-dichlorophenyl)-2-(1H-1,2,4-triazol-1-ylmethyl)-1,3-dioxolan-4-yl]methoxy phenyl]-4-isopropyl-piperazine (Tercanazole);
6-cyclohexyl-1-hydroxy-4-methyl-2(1H)-pyridone (ciclopirox);
and combinations thereof.

The anti-fungal agent 23 can be present in the therapeutic formulation 23 in any suitable and appropriate amount. For example, the anti-fungal agent 23 can be present up to about 15 wt. %, up to about 10 wt. % or up to about 5 wt. % of the therapeutic formulation 23. Alternatively, the anti-fungal agent 23 can be present in the therapeutic formulation 23 in those amount as disclosed, e.g., in the Physician's Desk Reference (PDR), 55th edition (2001).

The adhesive skin patch 1 can have any suitable size and shape. In addition, the adhesive skin patch 1 can be cut, as desired, to provide an adhesive skin patch 1 of a suitable size and shape. The adhesive skin patch 1 can be cut with any suitable cutting device such as a scissors, scalpel, or knife.

Typically, the adhesive skin patch 1 will have a length of about 0.1 inch to about 12 inches, about 0.1 inch to about 8 inches, of about 0.20 inch to about 4 inches, or about 0.2 inches to about 2.0 inches. Preferably, the adhesive skin patch 1 can have a length of about 1.0 inch to about 8 inches, about 2 inches to about 6 inches, or about 3 inches to about 4 inches.

Typically, the adhesive skin patch 1 will have a width of about 0.1 inch to about 12.0 inches, about 0.1 inch to about 4 inches, about 0.20 inches to about 2.0 inches, or about 0.2 inches to about 0.1 inch. Preferably, the adhesive skin patch 1 can have a width of about 1.0 inch to about 8 inches, about 2 inches to about 6 inches, or about 3 inches to about 4 inches.

Figure 7:
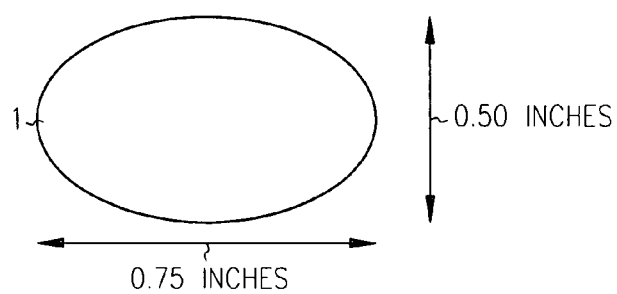

In one specific embodiment of the present invention, the adhesive skin patch 1 can be oval or elliptical in shape (see, FIG. 7). The oval or elliptical patch 1 can have a length of about 0.25 inches to about 0.50 inches and a width of about 0.25 inches to about 0.50 inches. See, FIG. 7. In another specific embodiment of the present invention, the adhesive skin patch 1 can have a circular shape. The circular patch 1 can have a diameter of about 0.25 inches to about 0.50 inches.

Figure 8:
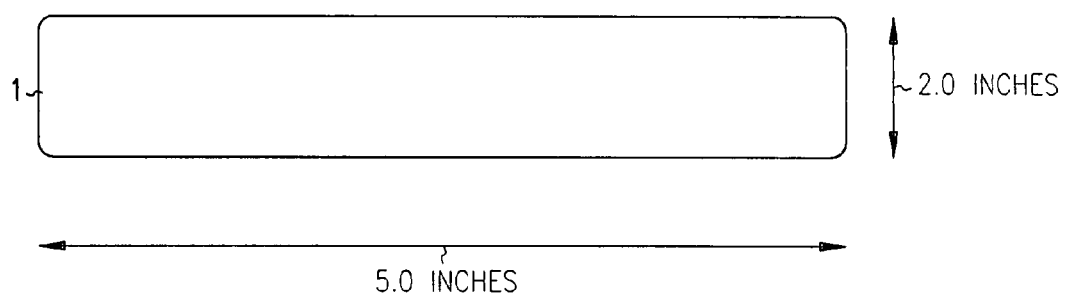

In another specific embodiment of the present invention, the adhesive skin patch 1 can be rectangular or square in shape (see, FIG. 8). The rectangular or square patch 1 can have a length of about 0.25 inches to about 8.0 inches and a width of about 0.25 inches to about 8.0 inches. For example, as shown in FIG. 8, the adhesive patch 1 can have a length of about 5.0 inches and a width of about 2.0 inches.

Preferably, the adhesive skin patch 1 can be individually wrapped. Some consumers have shown a preference for adhesive skin patches that are individually wrapped. The individually wrapped adhesive skin patch 1 offers to the consumer the ability and convenience of being able to carry a few (e.g., 1, 2, or 3) adhesive skin patches 1 that are each individually wrapped. In such an embodiment, the use of one patch will not compromise the cleanliness and/or sterility of the remaining patches. Alternatively, more than one adhesive skin patch 1 can be wrapped together. For example, 2 to about 20, 2 to about 15, or 2 to about 10 adhesive skin patches 1 can be wrapped together. The cost of such packaging and wrapping is decreased, compared to skin patches 1 that are individually wrapped. The cost of having two or more patches wrapped together is typically less expensive than skin patches 1 that are individually wrapped.

In one embodiment of the present invention, the adhesive patch 1 is sterile. The adhesive patch 1 can be sterilized by any suitable means known to those of skill in the art. For example, the adhesive patch 1 of the present invention can be sterilized by irradiation. Specifically, the adhesive patch 1 of the present invention can be sterilized by terminal irradiation (i.e., when the adhesive patch 1 of the present invention is in the package).

As shown in FIG. 9, the adhesive skin patch 1 can be applied to the skin surface of a patient. The adhesive skin patch 1 can be applied to any suitable skin surface of the patient. Suitable skin surfaces in which the patch can be applied include, e.g. below the eyes and above the neck. In one embodiment, the adhesive skin patch 1 can be applied to the lip of the patient or to the area between the upper lip and nose of the patient (as shown in FIG. 9). In another embodiment, the adhesive skin patch 1 can be applied to the upper arm of the patient (as shown in FIG. 11).

The patch of the present invention can treat a viral infection. As used herein, a viral infection refers to any disease caused by one of approximately 200 viruses pathogenic to humans. See, e.g., Mosby's Medical, Nursing & Allied Health Dictionary, 5th ed., Mosby, p. 1713(St. Louis, Mo.) 1998. The term virus refers to a group of microbes which with few exceptions are capable of passing through fine filters that retain most bacteria, and are incapable of growth or reproduction apart from living cells. They have a procaryotic genetic apparatus but differ sharply from bacteria in other respects. See, e.g., *Stedman's Medical Dictionary*, 25th Ed., illustrated, Williams & Wilkins, Baltimore, Md., pp. 1717-1723 (1990).

Specifically, the viral infection can be a cold sore, fever blister, chickenpox, shingles, or a canker sore. More specifically, the viral infection can be a cold sore, fever blister, chickenpox, or shingles. More specifically, the viral infection can be a cold sore, fever blister, or chickenpox. More specifically, the viral infection can be a cold sore or fever blister.

Alternatively, the viral infection can be caused by a vaccination. The vaccine can specifically be a member of the orthopox virus genus. Additionally, the vaccine can be a pox type virus, e.g., smallpox, cowpox, or monkeypox. In one embodiment of the present invention, the viral infection can be caused by smallpox vaccine made from live vaccinia virus. In another embodied of the present invention, the viral infection can be caused by the smallpox vaccine DRYVAX.

As used herein, "vaccination" refers to any injection of weakened bacteria given to protect against or to reduce the effects of related infectious diseases. Vaccinations are available to protect against many diseases, as typhoid, measles, smallpox, and mumps. Mosby's Medical Encyclopedia.

As used herein, "vaccine" refers to a liquid of weakened or dead germs given either by mouth, by injection into the muscle or under the skin, or into a muscle to protect against infectious disease. Some vaccines are grown in bird eggs, rabbit brains, or monkey kidneys, and the germs are killed or weakened with chemicals. Vaccines may be used one at a time or in combinations. Mosby's Medical Encyclopedia.

As used herein, "vaccinia" refers to an infectious disease of cattle caused by a virus that may be given to humans by direct contact or by deliberate injection as a protection against smallpox. A small bump develops at the place of infection. This is followed by a sick feeling and a fever that lasts for several days. After 2 weeks, the small bump forms a scab that drops off after a while, leaving a scar. The virus may be spread by scratching. Persons with eczema or other preexisting skin disease may develop widespread vaccinia. Rarely, a severe encephalitis follows vaccinia. Mosby's Medical Encyclopedia.

As used herein, "smallpox," or "variola," or "variola major" refers to a highly contagious virus-caused disease marked by fever, prostration, and a blisterlike rash. It is caused by one of two species of poxvirus. Because human beings are the only carrier for the viruses, worldwide vaccination with vaccinia, a related poxvirus, has been effective in wiping out smallpox. For several years no natural case of the disease has been known to occur. Mosby's Medical Encyclopedia.

As used herein, "exudate" refers to fluid, cells, or other substances that have been slowly discharged through small pores or breaks in cell membranes. Exudates can also include perspiration, pus, and serum.

As used herein, "cross-contamination" refers to a condition of being soiled, stained, touched, or exposed to harmful agents, as the entry of bacteria or viruses into a previously clean or sterile area from an area having been infected with the bacteria or viruses. For example, the cross-contamination can include the situation wherein a person receiving a smallpox vaccination allows the vaccinia virus from the vaccination site to come into contact with his/her fingers, and subsequently touches their mouth, eyes, any open wounds, etc.

In one embodiment of the present invention, the viral infection can include symptoms selected from the group of fever, malaise, head and body aches, vomiting, macules, papules, skin eruptions, vesicles, lesions, rash, sores, raised bumps that are optionally filled with a thick opaque fluid and optionally include a depression in the center of the raised bumps, scabs, pustules, swollen lymph glands, chills, topical pain, itching, topical tingling, a topical burning sensation, and combinations thereof.

In a specific embodiment of the present invention, the viral infection is caused by a smallpox vaccine. In such an embodiment, the skin surface having been vaccinated includes symptoms selected from the group of macules, papules, skin eruptions, vesicles, lesions, rash, sores, raised bumps that are optionally filled with a thick opaque fluid and optionally include a depression in the center of the raised bumps, scabs, pustules, topical pain, itching, topical tingling, a topical burning sensation, and combinations thereof.

The patch also relieves any topical discomfort typically encountered with viral infections. In addition, the patch can treat secondary infections that are typically encountered with viral infections. Moreover, the patch serves as a protective covering or barrier. Such protection serves to prevent or diminish the likelihood that foreign objects (e.g., a person's finger, clothing, etc.) will come into contact with the viral infection. This may effectively decrease the overall healing time of the viral infection. In addition, since a viral infection can be extremely contagious when a sore is present, the protective covering diminishes the likelihood that the virus will be passed from an infected individual to a non-infected individual. The patch also serves to absorb any exudate that typically accompanies the viral infection.

As used herein, "treating" or "treat" includes (i) preventing a pathologic condition (e.g., viral infection) from occurring (e.g. prophylaxis); (ii) inhibiting the pathologic condition (e.g., viral infection) or arresting its development; and (iii) relieving symptoms of the pathologic condition (e.g., viral infection).

Solute

As used herein, "solute" refers to any substance that when added to the therapeutic formulation, will increase the osmotic pressure. Specifically, the solute can increase the osmotic pressure of the therapeutic formulation to above about 308 mOsmol/L.

Any suitable solute can be employed herein, provided the solute effectively increases the osmotic pressure of the therapeutic formulation to above about 308 mOsmol/L. Suitable solutes include, e.g., a carbohydrate, a water-soluble salt, a weak acid, a weak base, a monohydric alcohol, a polyhydric alcohol, a water-soluble amino acid, a liquid-soluble protein, or a combination thereof. Suitable specific solutes include, e.g., sodium chloride, potassium chloride, calcium chloride, calcium carbonate, sucrose, glucose, levulose, lactose, acetic acid, adipid acid, aspartic acid, glutamic acid, malic acid, potassium bicarbonate, sodium bicarbonate, albumin, casein, glycine, alanine, cysteine, leucine, ethanol, methanol, glycerin, ethylene glycol, propylene glycol, or a combination thereof. Additional suitable solutes are disclosed, e.g., in U.S. Pat. No. 6,348,212.

The solute can be employed in any suitable and appropriate amount, provided the solute effectively increases the osmotic pressure of the therapeutic formulation to above about 308 mOsmol/L. Typically, when present, the solute will be employed up to about 50 wt. % of the therapeutic formulation, up to about 25 wt. % of the therapeutic formulation, or up to about 15 wt. % of the therapeutic formulation. In one embodiment of the present invention, the solute can be employed in about 0.1 wt % to about 15 wt. % of the therapeutic formulation. Additional suitable amounts that the one or more solutes can be employed are disclosed, e.g., in U.S. Pat. No. 6,348,212.

Upon placing the adhesive patch, with a solute present in the therapeutic formulation, on a skin surface having raised bumps that are filled with a thick opaque fluid, fluid contained in the raised bumps is effectively transported by osmotic pressure into the therapeutic formulation of the adhesive patch. As a result, accumulated fluid contained in the raised bumps is reduced, while keeping the epidermis intact. Additionally, the likelihood of breaking the raised bumps and releasing virus laden fluid is diminished.

In such an embodiment of the present invention, the adhesive patch covers a skin surface having raised bumps that are filled with a thick opaque fluid, e.g., a skin surface that has recently been vaccinated with smallpox. The fluid volume within the raised bumps is significantly reduced. This reduction results from placing a hypertonic hydrogel layer (i.e., therapeutic formulation) in direct contact with the raised bumps so as to produce an osmotic imbalance between the fluid within the raised bumps and the hydrogel. After the patch has been applied, the fluid is drawn out of the raised bumps by osmotic force through the raised epidermis which, upon being hydrated externally by the therapeutic formulation, can then act as a semi-permeable membrane. The structural integrity of the epidermis remains intact due to the protection provided by the patch. Following this, the epidermis will lay down on the dermis. It was found that the epidermis will then heal to the dermis without pain like a split thickness skin graft. Thus, one embodiment of the present invention provides a means of reducing the thick opaque fluid contained in raised bumps on a skin surface that has recently been vaccinated with smallpox. The osmotic imbalance persists while the patch is in place and continues to draw fluid from the low concentration in the raised bumps to the high concentration in the hypertonic hydrogel. The hydrogel layer, i.e., therapeutic formulation, forms a water bridge between itself and the outer surface of the skin that makes up the top of the raised bumps. This bridge allows the flow of fluid from within the raised bumps, which has a lower osmotic pressure than the osmotic pressure in the hydrogel layer.

The invention will now be illustrated by the following non-limiting Examples.

EXAMPLES

Example 1

Therapeutic Formulation (in wt. %)

| Component | Specific Embodiment (Weight %) |
|---|---|
| Glycerin | 48.2 |
| Lysine | 2.0 |
| Propylene Glycol | 2.0 |
| Eucalyptus Oil | 1.6 |
| Adhesives | 3.0 |
| Lidocaine | 3.8 |
| Aloe Vera Gel 10X | 0.5 |
| Karaya | 26.0 |
| Deionized Water | 10.5 |
| Quat-15 | 0.1 |

-continued

| Component | Specific Embodiment (Weight %) |
|---|---|
| Camphor | 2.0 |
| Vitamin E | 0.3 |
| Total | 100.0 |

Example 2

Therapeutic Formulation (in wt. %)

| Component | Specific Embodiment (Weight %) |
|---|---|
| Adhesives | 11.00 |
| Aloe Vera, 10X | 0.50 |
| Eucalyptus Oil | 1.60 |
| Glycerin | 48.07 |
| Karaya | 28.00 |
| Benzocaine | 5.00 |
| Triethylene Glycol | 3.00 |
| Q-15 | 0.03 |
| Vitamin E Acetate | 0.30 |
| Water | 4.50 |
| Total | 100.0 |

Example 3

Therapeutic Formulation (in wt. %)

| Component | Specific Embodiment (Weight %) |
|---|---|
| Adhesives | 7.00 |
| Aloe Vera, 10X | 0.50 |
| Menthol | 0.50 |
| Vaseline Fragrance | 2.00 |
| Glycerin | 48.27 |
| Karaya | 26.90 |
| Lidocaine | 4.00 |
| Lysine Hydrochloride | 2.00 |
| Propylene Glycol | 2.00 |
| Q-15 | 0.03 |
| Vitamin E Acetate | 0.30 |
| Water | 6.50 |
| Total | 100.0 |

Example 4

Therapeutic Formulation (in wt. %)

| Component | Specific Embodiment (Weight %) |
| --- | --- |
| Adhesives | 4.00 |
| Aloe Vera, 10X | 0.50 |
| Bacitracin | 0.70 |
| Camphor | 2.00 |
| Eucalyptus Oil | 1.60 |
| Glycerin | 47.57 |
| Karaya | 26.00 |
| Lidocaine | 3.80 |
| Lysine Hydrochloride | 2.00 |
| Propylene Glycol | 2.00 |
| Q-15 | 0.03 |
| Vitamin E Acetate | 0.30 |
| Water | 9.50 |
| Total | 100.0 |

Example 5

Therapeutic Formulation (in wt. %)

| Component | Specific Embodiment (Weight %) |
| --- | --- |
| Adhesives | 10.00 |
| Aloe Vera, 10X | 0.50 |
| Camphor | 2.00 |
| Eucalyptus Oil | 1.60 |
| Glycerin | 44.07 |
| Karaya | 26.00 |
| Benzocaine | 5.00 |
| Lysine Hydrochloride | 2.00 |
| Triethylene Glycol | 5.00 |
| Q-15 | 0.03 |
| Vitamin E Acetate | 0.30 |
| Water | 3.50 |
| Total | 100.0 |

Example 6

Therapeutic Formulation (in wt. %)

| Component | Specific Embodiment (Weight %) |
| --- | --- |
| Adhesives | 10.00 |
| Aloe Vera, 10X | 0.50 |
| Menthol | 0.50 |
| Vaseline Fragrance | 2.00 |
| Glycerin | 44.27 |
| Karaya | 26.90 |
| Benzocaine | 5.00 |
| Acyclovir | 2.00 |
| Triethylene Glycol | 5.00 |
| Q-15 | 0.03 |
| Vitamin E Acetate | 0.30 |
| Water | 3.50 |
| Total | 100.0 |

Example 7

Therapeutic Formulation (in wt. %)

| Component | Specific Embodiment (Weight %) |
| --- | --- |
| Adhesives | 2.00 |
| Aloe Vera, 1X | 0.50 |
| Bacitracin | 0.70 |
| Camphor | 2.00 |
| Eucalyptus Oil | 1.60 |
| Glycerin | 43.37 |
| Karaya | 26.00 |
| Benzocaine | 5.00 |
| Lysine Hydrochloride | 2.00 |
| Triethylene Glycol | 5.00 |
| Q-15 | 0.03 |
| Vitamin E Acetate | 0.30 |
| Water | 11.50 |
| Total | 100.0 |

Example 8

Therapeutic Formulation (in wt. %)

| Component | Specific Embodiment (Weight %) |
| --- | --- |
| Adhesives | 2.00 |
| Aloe Vera, 1X | 0.50 |
| Eucalyptus Oil | 1.60 |
| Glycerin | 50.07 |
| Karaya | 26.00 |
| Lidocaine | 4.00 |
| Lysine Hydrochloride | 2.00 |
| Propylene Glycol | 2.00 |
| Q-15 | 0.03 |
| Vitamin E Acetate | 0.30 |
| Water | 11.50 |
| Total | 100.0 |

Example 9

Therapeutic Formulation (in wt. %)

| Component | Specific Embodiment (Weight %) |
|---|---|
| Adhesives | 3.00 |
| Aloe Vera, 1X | 0.50 |
| Vaseline Fragrance | 2.00 |
| Glycerin | 48.77 |
| Karaya | 26.90 |
| Lidocaine | 4.00 |
| Acyclovir | 2.00 |
| Propylene Glycol | 2.00 |
| Q-15 | 0.03 |
| Vitamin E Acetate | 0.30 |
| Water | 10.50 |
| Total | 100.0 |

Example 10

Therapeutic Formulation (in wt. %)

| Component | Specific Embodiment (Weight %) |
|---|---|
| Adhesives | 6.00 |
| Aloe Vera, 1X | 0.50 |
| Eucalyptus Oil | 1.60 |
| Glycerin | 49.07 |
| Karaya | 26.00 |
| Lidocaine | 4.00 |
| Lysine | 2.00 |
| Triethylene Glycol | 3.00 |
| Q-15 | 0.03 |
| Vitamin E Acetate | 0.30 |
| Water | 7.50 |
| Total | 100.0 |

Example 11

Therapeutic Formulation (in wt. %

| Component | Specific Embodiment (Weight %) |
|---|---|
| Adhesives | 8.00 |
| Aloe Vera, 1X | 0.50 |
| Eucalyptus Oil | 1.60 |
| Glycerin | 49.07 |
| Karaya | 26.00 |
| Benzocaine | 5.00 |
| Lysine Hydrochloride | 2.00 |
| Propylene Glycol | 2.00 |
| Q-15 | 0.03 |
| Vitamin E Acetate | 0.30 |
| Water | 5.50 |
| Total | 100.0 |

Example 12

Therapeutic Formulation (in wt. %)

| Component | Specific Embodiment (Weight %) |
|---|---|
| Adhesives | 12.00 |
| Aloe Vera, 1X | 0.50 |
| Vaseline Fragrance | 2.00 |
| Glycerin | 47.77 |
| Karaya | 26.90 |
| Benzocaine | 5.00 |
| Acyclovir | 2.00 |
| Propylene Glycol | 2.00 |
| Q-15 | 0.03 |
| Vitamin E Acetate | 0.30 |
| Water | 1.50 |
| Total | 100.0 |

Example 13

Therapeutic Formulation (in wt. %)

| Component | Specific Embodiment (Weight %) |
|---|---|
| Adhesives | 12.00 |
| Aloe Vera, 1X | 0.50 |
| Eucalyptus Oil | 1.60 |
| Glycerin | 48.07 |
| Karaya | 26.00 |
| Benzocaine | 5.00 |
| Lysine | 2.00 |
| Triethylene Glycol | 3.00 |
| Q-15 | 0.03 |
| Vitamin E Acetate | 0.30 |
| Water | 1.50 |
| Total | 100.0 |

Example 14

Therapeutic Formulation (in wt. %)

| Component | Specific Embodiment (Weight %) |
|---|---|
| Adhesives | 11.00 |
| Aloe Vera, 1X | 0.50 |
| Eucalyptus Oil | 1.60 |
| Glycerin | 50.07 |
| Karaya | 28.00 |
| Lidocaine | 4.00 |
| Propylene Glycol | 2.00 |
| Q-15 | 0.03 |
| Vitamin E Acetate | 0.30 |
| Water | 2.50 |
| Total | 100.0 |

Example 15

Therapeutic Formulation (in wt. %)

| Component | Specific Embodiment (Weight %) |
|---|---|
| Adhesives | 8.00 |
| Aloe Vera, 1X | 0.50 |
| Vaseline Fragrance | 2.00 |
| Glycerin | 48.77 |
| Karaya | 28.90 |
| Lidocaine | 4.00 |
| Propylene Glycol | 2.00 |
| Q-15 | 0.03 |
| Vitamin E Acetate | 0.30 |
| Water | 5.50 |
| Total | 100.0 |

Example 16

Therapeutic Formulation (in wt. %)

| Component | Specific Embodiment (Weight %) |
|---|---|
| Adhesives | 11.00 |
| Aloe Vera, 1X | 0.50 |
| Eucalyptus Oil | 1.60 |
| Glycerin | 49.07 |
| Karaya | 28.00 |
| Lidocaine | 4.00 |
| Triethylene Glycol | 3.00 |
| Q-15 | 0.03 |
| Vitamin E Acetate | 0.30 |
| Water | 2.50 |
| Total | 100.0 |

Example 17

Therapeutic Formulation (in wt. %)

| Component | Specific Embodiment (Weight %) |
|---|---|
| Adhesives | 9.00 |
| Aloe Vera, 1X | 0.50 |
| Eucalyptus Oil | 1.60 |
| Glycerin | 49.07 |
| Karaya | 28.00 |
| Benzocaine | 5.00 |
| Propylene Glycol | 2.00 |
| Q-15 | 0.03 |
| Vitamin E Acetate | 0.30 |
| Water | 5.50 |
| Total | 100.0 |

Example 18

Therapeutic Formulation (in wt. %)

| Component | Specific Embodiment (Weight %) |
|---|---|
| Adhesives | 9.00 |
| Aloe Vera, 1X | 0.50 |
| Vaseline Fragrance | 2.00 |
| Glycerin | 47.77 |
| Karaya | 28.90 |
| Benzocaine | 5.00 |
| Propylene Glycol | 2.00 |
| Q-15 | 0.03 |
| Vitamin E Acetate | 0.30 |
| Water | 5.50 |
| Total | 100.0 |

Example 19

Therapeutic Formulation (in wt. %)

| Component | Specific Embodiment (Weight %) |
|---|---|
| Adhesives | 4.00 |
| Aloe Vera, 10X | 0.50 |
| Camphor | 2.00 |
| Eucalyptus Oil | 1.60 |
| Glycerin | 48.27 |
| Karaya | 26.00 |
| Lidocaine | 3.80 |
| Lysine Hydrochloride | 2.00 |
| Propylene Glycol | 2.00 |
| Q-15 | 0.03 |
| Vitamin E Acetate | 0.30 |
| Water | 9.50 |
| Total | 100.0 |

Example 20

Therapeutic Formulation (in wt. %)

| Component | Specific Embodiment (Weight %) |
|---|---|
| Adhesives | 6.00 |
| Aloe Vera, 10X | 0.50 |
| Eucalyptus Oil | 1.60 |
| Glycerin | 49.07 |
| Karaya | 28.00 |
| Camphor | 3.00 |
| Propylene Glycol | 2.00 |
| Q-15 | 0.03 |
| Vitamin E Acetate | 0.30 |
| Water | 9.50 |
| Total | 100.0 |

Example 21

Therapeutic Formulation (in wt. %)

| Component | Specific Embodiment (Weight %) |
|---|---|
| Adhesives | 10.00 |
| Aloe Vera, 10X | 0.50 |
| Vaseline Fragrance | 2.00 |
| Glycerin | 47.77 |
| Karaya | 28.90 |
| Menthol | 1.00 |
| Propylene Glycol | 2.00 |
| Q-15 | 0.03 |
| Vitamin E Acetate | 0.30 |
| Water | 9.50 |
| Total | 100.0 |

Example 22

Therapeutic Formulation (in wt. %)

| Component | Specific Embodiment (Weight %) |
|---|---|
| Adhesives | 6.00 |
| Aloe Vera, 10X | 0.50 |
| Eucalyptus Oil | 1.60 |
| Glycerin | 48.07 |
| Karaya | 28.00 |
| Camphor | 3.00 |
| Triethylene Glycol | 3.00 |
| Q-15 | 0.03 |
| Vitamin E Acetate | 0.30 |
| Water | 9.50 |
| Total | 100.0 |

Example 23

Therapeutic Formulation (in wt. %)

| Component | Specific Embodiment (Weight %) |
|---|---|
| Adhesives | 8.30 |
| Aloe Vera, 10X | 0.50 |
| Eucalyptus Oil | 1.60 |
| Glycerin | 49.07 |
| Karaya | 28.00 |
| Bacitracin | 0.70 |
| Propylene Glycol | 2.00 |
| Q-15 | 0.03 |
| Vitamin E Acetate | 0.30 |
| Water | 9.50 |
| Total | 100.0 |

Example 24

Therapeutic Formulation (in wt. %)

| Component | Specific Embodiment (Weight %) |
|---|---|
| Adhesives | 8.00 |
| Aloe Vera, 10X | 0.50 |
| Vaseline Fragrance | 2.00 |
| Glycerin | 47.77 |
| Karaya | 28.90 |
| Neomycin | 1.00 |
| Propylene Glycol | 2.00 |
| Q-15 | 0.03 |
| Vitamin E Acetate | 0.30 |
| Water | 9.50 |
| Total | 100.0 |

Example 25

Therapeutic Formulation (in wt. %)

| Component | Specific Embodiment (Weight %) |
|---|---|
| Adhesives | 8.30 |
| Aloe Vera, 10X | 0.50 |
| Eucalyptus Oil | 1.60 |
| Glycerin | 48.07 |
| Karaya | 28.00 |
| Bacitracin | 0.70 |
| Triethylene Glycol | 3.00 |
| Q-15 | 0.03 |
| Vitamin E Acetate | 0.30 |
| Water | 9.50 |
| Total | 100.0 |

Example 26

Therapeutic Formulation (in wt. %)

| Component | Specific Embodiment (Weight %) |
|---|---|
| Adhesives | 10.00 |
| Aloe Vera, 10X | 0.50 |
| Camphor | 2.00 |
| Eucalyptus Oil | 1.60 |
| Glycerin | 48.30 |
| PAAM | 20.00 |
| Lidocaine | 3.80 |
| Lysine Hydrochloride | 2.00 |
| Propylene Glycol | 2.00 |
| Vitamin E Acetate | 0.30 |
| Water | 9.50 |
| Total | 100.0 |

Example 27

Therapeutic Formulation (in wt. %)

| Component | Specific Embodiment (Weight %) |
|---|---|
| Adhesives | 10.00 |
| Aloe Vera, 10X | 0.50 |
| Menthol | 0.50 |
| Vaseline Fragrance | 2.00 |
| Glycerin | 48.30 |
| PAAM | 20.90 |
| Lidocaine | 4.00 |
| Acyclovir | 2.00 |
| Propylene Glycol | 2.00 |
| Vitamin E Acetate | 0.30 |
| Water | 9.50 |
| Total | 100.0 |

Example 28

Therapeutic Formulation (in wt. %)

| Component | Specific Embodiment (Weight %) |
|---|---|
| Adhesives | 10.00 |
| Aloe Vera, 10X | 0.50 |
| Bacitracin | 0.70 |
| Camphor | 2.00 |
| Eucalyptus Oil | 1.60 |
| Glycerin | 47.60 |
| PAAM | 20.00 |
| Lidocaine | 3.80 |
| Lysine | 2.00 |
| Propylene Glycol | 2.00 |
| Vitamin E Acetate | 0.30 |
| Water | 9.50 |
| Total | 100.0 |

Example 29

Therapeutic Formulation (in wt. %)

| Component | Specific Embodiment (Weight %) |
|---|---|
| Adhesives | 10.00 |
| Aloe Vera, 1X | 0.50 |
| Camphor | 2.00 |
| Eucalyptus Oil | 1.60 |
| Glycerin | 44.10 |
| PAAM | 20.00 |
| Benzocaine | 5.00 |
| Acyclovir | 2.00 |
| Triethylene Glycol | 5.00 |
| Vitamin E Acetate | 0.30 |
| Water | 9.50 |
| Total | 100.0 |

Example 30

Therapeutic Formulation (in wt. %)

| Component | Specific Embodiment (Weight %) |
|---|---|
| Adhesives | 10.00 |
| Aloe Vera, 1X | 0.50 |
| Menthol | 0.50 |
| Vaseline Fragrance | 2.00 |
| Glycerin | 44.30 |
| PAAM | 20.90 |
| Benzocaine | 5.00 |
| Acyclovir | 2.00 |
| Triethylene Glycol | 5.00 |
| Vitamin E Acetate | 0.30 |
| Water | 9.50 |
| Total | 100.0 |

Example 31

Therapeutic Formulation (in wt. %)

| Component | Specific Embodiment (Weight %) |
|---|---|
| Adhesives | 10.00 |
| Aloe Vera, 1X | 0.50 |
| Bacitracin | 0.70 |
| Camphor | 2.00 |

-continued

| Component | Specific Embodiment (Weight %) |
|---|---|
| Eucalyptus Oil | 1.60 |
| Glycerin | 43.40 |
| PAAM | 20.00 |
| Benzocaine | 5.00 |
| Lysine | 2.00 |
| Triethylene Glycol | 5.00 |
| Vitamin E Acetate | 0.30 |
| Water | 9.50 |
| Total | 100.0 |

Example 32

Therapeutic Formulation (in wt. %)

| Component | Specific Embodiment (Weight %) |
|---|---|
| Adhesives | 4.00 |
| Aloe Vera, 1X | 0.50 |
| Eucalyptus Oil | 1.60 |
| Glycerin | 50.07 |
| PAAM | 26.03 |
| Lidocaine | 4.00 |
| Lysine Hydrochloride | 2.00 |
| Propylene Glycol | 2.00 |
| Vitamin E Acetate | 0.30 |
| Water | 9.50 |
| Total | 100.0 |

Example 33

Therapeutic Formulation (in wt. %)

| Component | Specific Embodiment (Weight %) |
|---|---|
| Adhesives | 6.00 |
| Aloe Vera, 1X | 0.50 |
| Vaseline Fragrance | 2.00 |
| Glycerin | 48.77 |
| PAAM | 26.93 |
| Lidocaine | 4.00 |
| Acyclovir | 2.00 |
| Propylene Glycol | 2.00 |
| Vitamin E Acetate | 0.30 |
| Water | 7.50 |
| Total | 100.0 |

Example 34

Therapeutic Formulation (in wt. %)

| Component | Specific Embodiment (Weight %) |
|---|---|
| Adhesives | 7.00 |
| Aloe Vera, 1X | 0.50 |
| Eucalyptus Oil | 1.60 |
| Glycerin | 49.07 |
| PAAM | 26.03 |
| Lidocaine | 4.00 |
| Lysine | 2.00 |
| Triethylene Glycol | 3.00 |
| Vitamin E Acetate | 0.30 |
| Water | 6.50 |
| Total | 100.0 |

Example 35

Therapeutic Formulation (in wt. %)

| Component | Specific Embodiment (Weight %) |
|---|---|
| Adhesives | 4.00 |
| Aloe Vera, 1X | 0.50 |
| Eucalyptus Oil | 1.60 |
| Glycerin | 49.07 |
| PAAM | 26.03 |
| Benzocaine | 5.00 |
| Lysine Hydrochloride | 2.00 |
| Propylene Glycol | 2.00 |
| Vitamin E Acetate | 0.30 |
| Water | 9.50 |
| Total | 100.0 |

Example 36

Therapeutic Formulation (in wt. %)

| Component | Specific Embodiment (Weight %) |
|---|---|
| Adhesives | 4.00 |
| Aloe Vera, 10X | 0.50 |
| Vaseline Fragrance | 2.00 |
| Glycerin | 47.80 |
| PAAM | 26.90 |
| Benzocaine | 5.00 |
| Acyclovir | 2.00 |
| Propylene Glycol | 2.00 |
| Vitamin E Acetate | 0.30 |
| Water | 9.50 |
| Total | 100.0 |

Example 37

Therapeutic Formulation (in wt. %)

| Component | Specific Embodiment (Weight %) |
|---|---|
| Adhesives | 8.00 |
| Aloe Vera, 10X | 0.50 |
| Eucalyptus Oil | 1.60 |
| Glycerin | 48.10 |
| PAAM | 26.00 |
| Benzocaine | 5.00 |
| Lysine | 2.00 |
| Triethylene Glycol | 3.00 |
| Vitamin E Acetate | 0.30 |
| Water | 5.50 |
| Total | 100.0 |

Example 38

Therapeutic Formulation (in wt. %)

| Component | Specific Embodiment (Weight %) |
|---|---|
| Adhesives | 8.00 |
| Aloe Vera, 10X | 0.50 |
| Eucalyptus Oil | 1.60 |
| Glycerin | 50.07 |
| PAAM | 28.03 |
| Lidocaine | 4.00 |
| Propylene Glycol | 2.00 |
| Vitamin E Acetate | 0.30 |
| Water | 5.50 |
| Total | 100.0 |

Example 39

Therapeutic Formulation (in wt. %)

| Component | Specific Embodiment (Weight %) |
|---|---|
| Adhesives | 8.00 |
| Aloe Vera, 10X | 0.50 |
| Vaseline Fragrance | 2.00 |
| Glycerin | 48.77 |
| PAAM | 28.93 |
| Lidocaine | 4.00 |
| Propylene Glycol | 2.00 |
| Vitamin E Acetate | 0.30 |
| Water | 5.50 |
| Total | 100.0 |

Example 40

Therapeutic Formulation (in wt. %)

| Component | Specific Embodiment (Weight %) |
|---|---|
| Adhesives | 8.00 |
| Aloe Vera, 10X | 0.50 |
| Eucalyptus Oil | 1.60 |
| Glycerin | 49.07 |
| PAAM | 28.03 |
| Lidocaine | 4.00 |
| Triethylene Glycol | 3.00 |
| Vitamin E Acetate | 0.30 |
| Water | 5.50 |
| Total | 100.0 |

Example 41

Therapeutic Formulation (in wt. %)

| Component | Specific Embodiment (Weight %) |
|---|---|
| Adhesives | 8.00 |
| Aloe Vera, 10X | 0.50 |
| Eucalyptus Oil | 1.60 |
| Glycerin | 49.07 |
| PAAM | 28.03 |
| Benzocaine | 5.00 |
| Propylene Glycol | 2.00 |
| Vitamin E Acetate | 0.30 |
| Water | 5.50 |
| Total | 100.0 |

Example 42

Therapeutic Formulation (in wt. %)

| Component | Specific Embodiment (Weight %) |
|---|---|
| Adhesives | 8.00 |
| Aloe Vera, 10X | 0.50 |
| Vaseline Fragrance | 2.00 |
| Glycerin | 47.80 |
| PAAM | 28.90 |
| Benzocaine | 5.00 |
| Propylene Glycol | 2.00 |
| Vitamin E Acetate | 0.30 |
| Water | 5.50 |
| Total | 100.0 |

Example 43

Therapeutic Formulation (in wt. %)

| Component | Specific Embodiment (Weight %) |
|---|---|
| Adhesives | 4.00 |
| Aloe Vera, 10X | 0.50 |
| Eucalyptus Oil | 1.60 |
| Glycerin | 48.10 |
| PAAM | 28.00 |
| Benzocaine | 5.00 |
| Triethylene Glycol | 3.00 |
| Vitamin E Acetate | 0.30 |
| Water | 9.50 |
| Total | 100.0 |

Example 44

Therapeutic Formulation (in wt. %)

| Component | Specific Embodiment (Weight %) |
|---|---|
| Adhesives | 6.00 |
| Aloe Vera, 10X | 0.50 |
| Eucalyptus Oil | 1.60 |
| Glycerin | 49.07 |
| PAAM | 28.03 |
| Camphor | 3.00 |
| Propylene Glycol | 2.00 |
| Vitamin E Acetate | 0.30 |
| Water | 9.50 |
| Total | 100.0 |

Example 45

Therapeutic Formulation (in wt. %)

| Component | Specific Embodiment (Weight %) |
|---|---|
| Adhesives | 8.00 |
| Aloe Vera, 10X | 0.50 |
| Vaseline Fragrance | 2.00 |
| Glycerin | 47.80 |
| PAAM | 28.90 |
| Menthol | 1.00 |
| Propylene Glycol | 2.00 |
| Vitamin E Acetate | 0.30 |
| Water | 9.50 |
| Total | 100.0 |

Example 46

Therapeutic Formulation (in wt. %)

| Component | Specific Embodiment (Weight %) |
|---|---|
| Adhesives | 6.00 |
| Aloe Vera, 10X | 0.50 |
| Eucalyptus Oil | 1.60 |
| Glycerin | 48.10 |
| PAAM | 28.00 |
| Camphor | 3.00 |
| Triethylene Glycol | 3.00 |
| Vitamin E Acetate | 0.30 |
| Water | 9.50 |
| Total | 100.0 |

Example 47

Therapeutic Formulation (in wt. %)

| Component | Specific Embodiment (Weight %) |
|---|---|
| Adhesives | 8.30 |
| Aloe Vera, 10X | 0.50 |
| Eucalyptus Oil | 1.60 |
| Glycerin | 49.07 |
| PAAM | 28.03 |
| Bacitracin | 0.70 |
| Propylene Glycol | 2.00 |
| Vitamin E Acetate | 0.30 |
| Water | 9.50 |
| Total | 100.0 |

Example 48

Therapeutic Formulation (in wt. %)

| Component | Specific Embodiment (Weight %) |
|---|---|
| Adhesives | 8.00 |
| Aloe Vera, 10X | 0.50 |
| Vaseline Fragrance | 2.00 |
| Glycerin | 47.80 |
| PAAM | 28.90 |
| Neomycin | 1.00 |
| Propylene Glycol | 2.00 |
| Vitamin E Acetate | 0.30 |
| Water | 9.50 |
| Total | 100.0 |

Example 49

Therapeutic Formulation (in wt. %)

| Component | Specific Embodiment (Weight %) |
| --- | --- |
| Adhesives | 8.30 |
| Aloe Vera, 10X | 0.50 |
| Eucalyptus Oil | 1.60 |
| Glycerin | 48.10 |
| PAAM | 28.00 |
| Bacitracin | 0.70 |
| Triethylene Glycol | 3.00 |
| Vitamin E Acetate | 0.30 |
| Water | 9.50 |
| Total | 100.0 |

Example 50

Therapeutic Formulation (in wt. %)

| Component | Specific Embodiment (Weight %) |
| --- | --- |
| Adhesive | 15.00 |
| Glycerin | 30.00 |
| PAAM | 15.00 |
| PAA | 5.00 |
| Propylene Glycol | 20.00 |
| Water | 15.00 |

Example 51

Therapeutic Formulation (in wt. %)

| Component | Specific Embodiment (Weight %) |
| --- | --- |
| Adhesive | 15.00 |
| Glycerin | 30.00 |
| PAAM | 15.00 |
| PAA | 5.00 |
| Propylene Glycol | 24.00 |
| Griseofulvin | 1.00 |
| Water | 10.00 |

Example 52

Therapeutic Formulation (in wt. %)

| Component | Specific Embodiment (Weight %) |
| --- | --- |
| Glycerin | 32.00 |
| Polyquaternary amine | 37.00 |
| Propylene Glycol | 20.00 |
| Sodium Chloride | 1.00 |
| Water | 10.00 |

Example 53

Therapeutic Formulation (in wt. %)

| Component | Specific Embodiment (Weight %) |
| --- | --- |
| Tackifier comprising a vinyl acetate resin emulsion | 9.00 |
| Propylene Glycol | 33.00 |
| Water | 20.00 |
| Polyacrylamide | 15.00 |
| Sucrose | 11.00 |
| Maltodextrin | 12.00 |

Example 54

Therapeutic Formulation (in wt. %)

| Component | Specific Embodiment (Weight %) |
| --- | --- |
| Glycerol | 58.00 |
| Water | 10.00 |
| Polyacrylamide | 15.00 |
| Polyacrylic acid | 15.00 |
| Calcium chloride | 2.00 |

Example 55

Therapeutic Formulation (in wt. %)

| Component | Specific Embodiment (Weight %) |
| --- | --- |
| Propylene Glycol | 33.00 |
| Water | 20.00 |
| Polysulfonate | 15.00 |
| Sucrose | 11.00 |
| Maltodextrin | 12.00 |
| Tackifier comprising a vinyl acetate resin emulsion | 9.00 |

Example 56

Therapeutic Formulation (in wt. %)

| Component | Specific Embodiment (Weight %) |
|---|---|
| Propylene Glycol | 33.00 |
| Water | 20.00 |
| Carboxymethyl cellulose (CMC) | 15.00 |
| Sucrose | 11.00 |
| Maltodextrin | 12.00 |
| Tackifier comprising a vinyl acetate resin emulsion | 9.00 |

Example 57

Therapeutic Formulation (in wt. %)

| Component | Specific Embodiment (Weight %) |
|---|---|
| Adhesive | 15.00 |
| Glycerin | 25.00 |
| PAAM | 15.00 |
| PAA | 5.00 |
| Propylene Glycol | 19.00 |
| Water | 15.00 |
| Benzocaine | 2.00 |
| Menthol | 1.00 |
| Penicillin | 1.00 |
| Famciclovir | 1.00 |
| Calcium Chloride | 1.00 |

Example 58

Therapeutic Formulation (in wt. %)

| Componet | Specific Embodiment (Weight %) |
|---|---|
| Adhesive | 15.00 |
| Glycerin | 23.00 |
| PAAM | 15.00 |
| PAA | 5.00 |
| Propylene Glycol | 24.00 |
| Griseofulvin | 1.00 |
| Water | 10.00 |
| Lidocaine | 3.00 |
| Acyclovir | 1.00 |
| Sucrose | 3.00 |

Example 59

Therapeutic Formulation (in wt. %)

| Component | Specific Embodiment (Weight %) |
|---|---|
| Adhesive | 15.00 |
| Glycerin | 25.00 |
| PAAM | 15.00 |
| PAA | 5.00 |
| Propylene Glycol | 19.00 |
| Water | 15.00 |
| Benzocaine | 2.00 |
| Aloe Vera | 1.00 |
| Sulfamethoxazole | 1.00 |
| Famciclovir | 1.00 |
| Calcium Chloride | 1.00 |

Example 60

Therapeutic Formulation (in wt. %)

| Component | Specific Embodiment (Weight %) |
|---|---|
| Adhesive | 15.00 |
| Glycerin | 25.00 |
| PAAM | 15.00 |
| PAA | 5.00 |
| Propylene Glycol | 19.00 |
| Water | 15.00 |
| Lidocaine | 2.00 |
| Eucalyptus | 1.00 |
| Penicillin | 1.00 |
| Idoxuridine | 1.00 |
| Calcium Chloride | 1.00 |

The adhesive patch 1 of the present invention can be formulated or manufactured employing the above components. The adhesive patch 1 of the present invention can be formulated or manufactured using any suitable technique. Preferably, the adhesive patch 1 can be formulated or manufactured as described in U.S. Pat. No. 5,536,263; U.S. Pat. No. 5,741,510; and references cited therein; wherein the oil premix includes the antiviral agent 15, propylene glycol, and solvent 13; the glycerin premix includes glycerin, Vitamin E, and aloe vera gel; and the adhesive premix includes the adhesive, polymer 9, and water.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating a viral infection in a mammal in need thereof, wherein the viral infection is a viral infection associated with a smallpox vaccination at the vaccination site on the skin of the mammal, the method comprising applying to the skin surface of the mammal having been vaccinated a vapor-permeable adhesive patch comprising a backing of a flexible sheet of water insoluble material, the backing being vapor-permeable such that water vapor may diffuse therethrough, the backing having a front side and a back side and a therapeutic formulation positioned on at least a portion of the front side of the backing, positioned in at least a portion of the front side of the backing, or positioned on and in at least a portion of the front side of the backing, such that the therapeutic formulation penetrates the backing to an extent of about one fourth to about nine tenths of the thickness of the backing, wherein the therapeutic formulation comprises:

an antiviral agent;
a medicament useful for relieving topical discomfort;
an antimicrobial agent;
an adhesive; and
a solvent.

2. The method of claim 1 wherein the backing is porous.

3. The method of claim 1 wherein the backing is nonporous.

4. The method of claim 1 wherein the backing comprises a nonwoven fabric.

5. The method of claim 1 wherein the backing comprises polycellulose fibers, polyester fibers, polyurethane fibers, polyolefin fibers, polyamide fibers, cotton fibers, copolyester fibers, or any mixture thereof.

6. The method of claim 1 wherein upon contact with skin, the backing retains the therapeutic formulation and the patch allows moisture from the skin to pass through the patch.

7. The method of claim 1 wherein the backing comprises open cell foam.

8. The method of claim 7 wherein the open cell foam comprises polyurethane, polyvinyl chloride, polyethylene, or any combination thereof.

9. The method of claim 7 wherein upon contact with skin, the backing retains the therapeutic formulation and the patch allows moisture from the skin to pass through the patch.

10. The method of claim 1 wherein the antiviral agent is zinc, lysine, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, viracea2, cytovene, famciclovir, valaciclovir, penciclovir, hexadecyloxypropyl-cidofovir (HDP-CDV), nonoxynol-9, a pharmaceutically acceptable salt thereof, or any combination thereof.

11. The method of claim 1 wherein the antiviral agent is lysine hydrochloride.

12. The method of claim 11 wherein the lysine hydrochloride is present in about 0.01 wt. % to about 10 wt. % of the therapeutic formulation.

13. The method of claim 11 wherein the lysine hydrochloride is present in about 0.1 wt. % to about 4.0 wt. % of the therapeutic formulation.

14. The method of claim 1 wherein the medicament is an analgesic, anesthetic, antipruritic, or a combination thereof.

15. The method of claim 14 wherein the medicament is selected from camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, juniper tar, phenol, phenolate sodium, resorcinol, diphenhydramine hydrochloride, tripelennamine hydrochloride, hydrocortisone, hydrocortisone acetate, camphorated metacresol, carbolic acid, and combinations thereof.

16. The method of claim 15 wherein camphor is present in about 0.1 to about 3.0 wt. % of the therapeutic formulation, menthol is present in about 0.1 wt. % to about 1.0 wt. % of the therapeutic formulation, benzocaine is present in about 5.0 wt. % to about 20.0 wt. % of the therapeutic formulation, butamben picrate is present in about 1.0 wt. % of the therapeutic formulation, dibucaine is present in about 0.25 wt. % to about 1.0 wt. % of the therapeutic formulation, dibucaine hydrochloride is present in about 0.3 wt. % to about 0.5 wt. % of the therapeutic formulation, dimethisoquin hydrochloride is present in about 0.3 wt. % to about 0.5 wt. % of the therapeutic formulation, dyclonine hydrochloride is present in about 0.5 wt. % to about 1.0 wt. % of the therapeutic formulation, lidocaine is present in about 0.5 wt. % to about 4.0 wt. % of the therapeutic formulation, lidocaine hydrochloride is present in about 0.5 wt. % to about 4.0 wt. % of the therapeutic formulation, pramoxine hydrochloride is present in about 0.5 wt. % to about 1.0 wt. % of the therapeutic formulation, tetracaine is present in about 1.0 wt. % to about 2.0 wt. % of the therapeutic formulation, tetracaine hydrochloride is present in about 1.0 wt. % to about 2.0 wt. % of the therapeutic formulation, benzyl alcohol is present in about 10.0 wt. % to about 33.0 wt. % of the therapeutic formulation, juniper tar is present in about 1.0 wt. % to about 5.0 wt. % of the therapeutic formulation, phenolate sodium is present in about 0.5 wt. % to about 1.5 wt. % of the therapeutic formulation, resorcinol is present in about 0.5 wt. % to about 3.0 wt. % of the therapeutic formulation, diphenhydramine hydrochloride is present in about 1.0 wt. % to about 2.0 wt. % of the therapeutic formulation, tripelennamine hydrochloride is present in about 0.5 wt. % to about 2.0 wt. % of the therapeutic formulation, hydrocortisone is present in about 0.25 wt. % to about 1.0 wt. % of the therapeutic formulation, phenol is present in about 0.5 wt. % to about 1.5 wt. % of the therapeutic formulation, hydrocortisone acetate is present in about 0.25 wt. % to about 1.0 wt. % of the therapeutic formulation, camphorated metacresol is present such that camphor is present in about 3.0 wt. % to about 10.8 wt. % of the therapeutic formulation, metacresol is present in about 1.0 to about 3.6 wt. % of the therapeutic formulation, or any combination thereof.

17. The patch of claim 1 wherein the medicament useful for relieving topical discomfort is lidocaine.

18. The method of claim 17 wherein the lidocaine is present in about 0.5 wt. % to about 4.0 wt. % of the therapeutic formulation.

19. The method pf claim 1 wherein the medicament useful for relieving topical discomfort is camphor.

20. The method of claim 1 wherein the camphor is present in about 0.1 wt. % to about 3.0 wt. % of the therapeutic formulation.

21. The method of claim 1 wherein the antimicrobial agent is quat-15, a paraben, dichlorobenzyl alcohol, ethylene diamine tetreacetic acid, formaldehyde, gum benzoin, imidazolidinyl urea, phenyl-mercuric acetate, poly aminopropyl biguanide, propyl gallate, sorbic acid, cresol, chloroacetamide sodium benzoate, chloromethyl-methylisothiazolinone, chloromethyl-methylisothiazolon, chloromethyl-methylisothiazolinone benzalkonium chloride, an octylisothiazolinone benzimidazol-compound, chloromethyl-methylisothiazolinone octylisothiazolinone, o-phenylphenol benzisothiazolinone, o-phenylphenol benzisothiazolinone, benzisothiazolinone, an aliphatic amine of 2-thiopyridineoxide, benzoic acid, editic acid, phenolic acid, benzyl alcohol, isopropyl alcohol, benzenethonium chloride, bronopol, cetrimide, chlorhexidine, chlorobutanol, chlorocresol, phenol, phenoxyethanol, phenyl ethyl alcohol, phenylmercuric acetate, phenylmercuric borate, phenylmercuric nitrate, potassium sorbate, proplyene glycol, sodium benzoate, sodium propionate, thimerosol, a pharmaceutically acceptable salt thereof, or any combination thereof.

22. The method of claim 1 wherein the antimicrobial agent is quat-15.

23. The method of claim 22 wherein the quat-15 is present in about 0.01 wt. % to about 0.1 wt. % of the therapeutic formulation.

24. The method of claim 1 wherein the adhesive is an acrylic ester copolymer, a water-based adhesive, a hot melt adhesive, a pressure sensitive adhesive, a solvent based pressure sensitive adhesive, a polyacrylate, a polyisobutylene, a polybutene, a rubber, a silicone based pressure sensitive adhesive, a polystyrene-polybutadiene-polystyrene block polymer, a polystyrene-polyisoprene-polystyrene block polymer, a polystyrene-poly(ethylene-butylene)-polystyrene block polymer, or any combination thereof.

25. The method of claim 1 wherein the adhesive is an acrylic ester copolymer.

26. The method of claim 25 wherein the acrylic ester copolymer is present in about 0.5 wt. % to about 8.0 wt. % of the therapeutic formulation.

27. The method of claim 1 wherein the solvent comprises water; triethylene glycol; ethylene glycol; glycerin; propylene glycol; triacetin; 1,3-propane diol; 2-methyl-1,3-propane diol; glycerol ricinoleate; PEG-6 caprylic/capric glycerides; caprylic/capric triglycerides; propyleneglycol dicaprylate/dicaprate; glycerol monostearate; glycerol monocaprylate; glycerol monolaurate; neopentyl alcohol; 1-hexadecanol; hydroxypropyl beta-cyclodextrin; vitamin E; vitamin E acetate; deoxycholic acid; taurodeoxycholic acid; 3-[(3-cholamidopropyl) dimethylammonio]-1-propane-sulfonate; cholic acid; cholesterol NF; propylene carbonate; lecithin; or a pharmaceutically acceptable salt thereof; or a combination thereof.

28. The method of claim 27 wherein the solvent comprises a $(C_1-C_{12})$acyclic hydrocarbon, a $(C_3-C_{12})$ cyclic hydrocarbon, a $(C_6-C_{12})$ aryl hydrocarbon, a $(C_6-C_{12})$ heteroaryl hydrocarbon, or a $(C_3-C_{12})$ heterocyclic hydrocarbon;

wherein any of the hydrocarbons can optionally include one or more carbon-carbon double bonds and any of the hydrocarbons can optionally include one or more carbon-carbon triple bonds;

wherein any of the hydrocarbons can optionally include one or more oxy (—O—), carbonyl (—C(═O)C—), carboxylato (—C(═O)O—), dioxy (—O—O—), dithio (—S—S—), imino (—NH—), methylene dioxy (—$OCH_2O$—), sulfinyl (—SO—), sulfonyl (—$SO_2$—), or thio (—S—); and wherein any of the hydrocarbons can optionally be substituted with one or more amino, hydroxyl, cyano, nitro, $(C_1-C_{12})$alkoxy, halo, trifluoro, trifluoro $(C_1-C_{12})$ alkyl, $NR^1R^2$, or $COOR^1$; wherein $R^1$ and $R^2$ are each independently hydrogen, a $(C_1-C_{12})$ acyclic hydrocarbon or a $(C_1-C_{12})$ cyclic hydrocarbon.

29. The method of claim 27 wherein the solvent is present in about 3.0 wt % to about 25.0 wt. % of the therapeutic formulation.

30. The method of claim 1 wherein the patch further comprising an anti-fungal agent.

31. The method of claim 30 wherein the anti-fungal agent comprises at least one of:

[1R-(1R*, 3S*, 5R*, 6R*, 9R*, 11R*, 15S*, 16R*, 17R*, 18S*, 19E, 21E, 23E, 25E, 27E, 29E, 31E, 33R*, 35S*, 36R*, 37S*)]-33-[(3-Amino-3,6-dideoxy-β-D-mannopyranosyl)oxy]-1,3,5,6,9,11,17,37-octahydroxy-15, 16,18-trimethyl-13-oxo-14,39-dioxabicyclo[33.3.1] nonatriaconta-19,21,23,25,27,29,31-heptaene-36-carboxylic acid (Amphotericin B); 5-fluorocytosine (Flucytosine); 2,4-difluoro-α,$\alpha^1$-bis(1H-1,2,4-triazol-1-ylmethyl) benzyl alcohol) (Fluconazole); griseofulvin microsize (Griseofulvin); (E)-N-(6,6-dimethyl-2-hepten-4-ynyl)-N-methyl-1-naphthalenemethanamine hydrochloride) (Terbinafine); cis-1-acetyl-4-[4-[(2-(2, 4-dichlorophenyl)-2-(1H-imadazol-1-ylmethyl)-1,3-dioxolan-4-yl]methoxyl]phenyl] piperazine (Ketoconazole); (±)-1-[(R*)-sec-butyl]-4-[p-[4-[p-[[(2R*,4S*)-2-(2,4-dichlorophenyl)-2-(1H-1,2,4-triazol-1-ylmethyl)-1,3-dioxolan-4-yl]methyoxy]phenyl]-1-piperazinyl] phenyl]-$\Delta^2$-1,2,4-triazolin-5-one mixture with (±)-1-[(R*)-sec-butyl]-4-[p-[4-[p-[[(2S*, 4R*)-2-(2,4-dichlorophenyl)-2-(H-1,2,4-triazol-1-ylmethyl)-1,3-dioxolan-4-yl]methoxy]phenyl]-1-piperazinyl] phenyl]-$\Delta^2$-1,2,4-triazolin-5-one or (±)-1-[(RS)-sec-butyl]-4-[p-[4-[p-[[(2R,4S)-2-(2,4-dichlorophenyl)-2-(1H-1,2,4-triazol-1-ylmethyl)-1,3-dioxolan-4-yl]-methoxy]phenyl]-1-piperazinyl]phenyl]-$\Delta^2$-1,2,4-triazolin-5-one (Itraconazole); 2-chloro-5-hydroxy-1, 3-dimethylbenzene (Chloroxylenol); griseofulvin ultramicrosize (Griseofulvin); 6-cyclohexyl-1-hydroxy-4-methyl-2(1H)-pyridinone (Ciclopirox); N-4-tert-butyl-benzyl-N-methyl-1-naphthalenemethylamine hydrochloride (Butenafine hydrochloride); nystatin; (E)-N-(Cinnamyl-N-methyl-1-naphthalenemethylamine hydrochloride (Naftifine hydrochloride); 1-(2,4-dichlorophenyl)-2-(1H-imidazol-1-yl)—O—[(2,4-dichlorophenyl)methyl]oxime, (Z)—, mononitrate (Oxiconazole nitrate); selenium sulfide; (±)-1-[4-(p-chlorophenyl)-2-[(2,6-dichlorophenyl)thio]butyl] imidazole mononitrate (Butoconazole nitrate); 1-(o-Chloro-α, α-diphenylbenzyl)imidazole (Clotrimazole); (cis-1-[p-[[2-(2,4-dichlorophenyl)-2-(1H-1,2,4-triazol-1-ylmethyl)-1,3-dioxolan-4-yl]methoxy phenyl]-4-isopropyl-piperazine (Tercanazole); 6-cyclohexyl-1-hydroxy-4-methyl-2(1H)-pyridone (ciclopirox); or combinations thereof.

32. The method of claim 1 wherein the patch is sterile.

33. The method of claim 32 wherein the patch is sterilized by irradiation.

34. The method of claim 32 wherein the patch is sterilized by terminal irradiation.

35. The method of claim 1 wherein the patch further comprising packaging material.

36. The method of claim 1 wherein upon placing the adhesive patch on a skin surface having raised bumps filled with a thick opaque fluid resulting from smallpox vaccination, fluid contained in the raised bumps is transported by osmotic pressure into the therapeutic formulation of the patch, thereby reducing accumulated fluid contained in the raised bumps, while keeping the epidermis intact.

37. The method of claim 36 wherein the therapeutic formulation is maintained in a hypertonic state relative to the raised bumps.

38. The method of claim 1 further comprising absorbing exudate from the viral infection by applying the patch to the skin surface of the mammal.

39. The method of claim 1 further comprising treating symptoms associated with the viral infection by applying the patch to the skin surface of the mammal.

40. The method of claim 1 further comprising treating a secondary bacterial infection associated with the viral infection by applying the patch to the skin surface of the mammal.

41. The method of claim 1 further comprising preventing cross-contamination of the viral infection from the vaccination site by applying the patch to the skin surface of the mammal.

42. The method of claim 1 wherein the viral infection is caused by smallpox vaccine made from live vaccinia virus.

43. The method of claim 1 wherein the viral infection is caused by the smallpox vaccine DRYVAX.

* * * * *